(12) United States Patent
Cohen et al.

(10) Patent No.: US 7,196,056 B2
(45) Date of Patent: *Mar. 27, 2007

(54) PROTEIN-INDUCED MORPHOGENESIS OF KIDNEY TISSUE

(75) Inventors: Charles M. Cohen, Weston, MA (US); Kuber T. Sampath, Hollison, MA (US); Roy H. L. Pang, Etna, NH (US); Hermann Oppermann, Medway, MA (US); David C. Rueger, Hopkington, MA (US)

(73) Assignee: Curis, Inc., Cambridge, MA (US)

( * ) Notice: Subject to any disclaimer, the term of this patent is extended or adjusted under 35 U.S.C. 154(b) by 138 days.

This patent is subject to a terminal disclaimer.

(21) Appl. No.: 10/385,064

(22) Filed: Mar. 10, 2003

(65) Prior Publication Data

US 2004/0102373 A1    May 27, 2004

Related U.S. Application Data

(60) Continuation of application No. 09/464,206, filed on Dec. 15, 1999, now Pat. No. 6,531,445, which is a division of application No. 08/396,684, filed on Mar. 1, 1995, now abandoned, which is a continuation of application No. 08/091,395, filed on Jul. 13, 1993, now abandoned, which is a continuation of application No. 07/752,764, filed on Aug. 30, 1991, now abandoned, which is a continuation-in-part of application No. 07/667,274, filed on Mar. 11, 1991, now abandoned.

(51) Int. Cl.
*A61K 38/18* (2006.01)
*A61K 38/00* (2006.01)

(52) U.S. Cl. .............................. 514/2; 514/12
(58) Field of Classification Search ............... 514/2, 514/12; 424/85.1
See application file for complete search history.

(56) References Cited

U.S. PATENT DOCUMENTS

| | | |
|---|---|---|
| 4,721,096 A | 1/1988 | Naughton et al. |
| 4,861,757 A | 8/1989 | Antoniades et al. |
| 4,877,864 A | 10/1989 | Wang et al. |
| 4,919,939 A | 4/1990 | Baker |
| 4,935,497 A | 6/1990 | Veis et al. |
| 4,946,437 A | 8/1990 | Sredni et al. |
| 4,968,590 A | 11/1990 | Kuberasampath et al. |
| 4,975,526 A | 12/1990 | Kuberasampath et al. |
| 4,983,581 A | 1/1991 | Antoniades et al. |
| 5,002,488 A | 3/1991 | Homsy |
| 5,011,691 A | 4/1991 | Oppermann et al. |
| 5,013,649 A | 5/1991 | Wang et al. |
| 5,108,989 A | 4/1992 | Amento et al. |
| 5,124,316 A | 6/1992 | Antoniades et al. |
| 5,141,905 A | 8/1992 | Rosen et al. |
| 5,186,931 A | 2/1993 | Kishimoto et al. |
| 5,197,882 A | 3/1993 | Jernberg |
| 5,368,859 A | 11/1994 | Dunn et al. |
| 5,635,373 A | 6/1997 | Wozney et al. |
| 5,849,686 A | 12/1998 | Kuberasampath et al. |
| 6,034,062 A * | 3/2000 | Thies et al. .................... 514/12 |
| 6,090,776 A * | 7/2000 | Kuberasampath et al. ..... 514/2 |
| 6,194,376 B1 * | 2/2001 | Kuberasampath et al. ..... 514/2 |
| 6,288,031 B1 * | 9/2001 | Kuberasampath et al. .... 514/12 |
| 6,498,142 B1 * | 12/2002 | Sampath et al. .............. 514/12 |
| 6,861,404 B1 * | 3/2005 | Cohen et al. .................. 514/12 |
| 2004/0126375 A1 * | 7/2004 | Langenfeld .............. 424/145.1 |

FOREIGN PATENT DOCUMENTS

| | | |
|---|---|---|
| EP | 0148155 | 7/1985 |
| EP | 0416578 | 3/1991 |
| EP | 0495284 | 7/1992 |
| EP | 0 661 987 | 1/1998 |
| WO | WO 84/01106 | 3/1984 |
| WO | WO 88/00205 | 1/1988 |
| WO | WO 89/09787 | 10/1989 |
| WO | WO 89/09788 | 11/1989 |
| WO | WO 89/10409 | 11/1989 |
| WO | WO 89/11862 | 12/1989 |
| WO | WO 90/03733 | 4/1990 |
| WO | WO 90/10017 | 9/1990 |
| WO | WO 90/11366 | 10/1990 |
| WO | WO 91/05802 | 5/1991 |
| WO | WO 91/18558 | 12/1991 |
| WO | WO 92/00382 | 1/1992 |
| WO | WO 92/14481 | 9/1992 |
| WO | WO 92/15323 | 9/1992 |

(Continued)

OTHER PUBLICATIONS

Vukicevic et al., 1996, PNAS USA 93 :9021-9026.*

(Continued)

*Primary Examiner*—Elizabeth Kemmerer
(74) *Attorney, Agent, or Firm*—Fish & Neave IP Group, Ropes & Gray LLP

(57) ABSTRACT

Disclosed are 1) amino acid sequence data, structural features, homologies and various other data characterizing morphogenic proteins, 2) methods of producing these proteins from natural and recombinant sources and from synthetic constructs, 3) morphogenic devices comprising these morphogenic proteins and a suitably modified tissue-specific matrix, and 4) methods of inducing non-chondrogenic tissue growth in a mammal.

8 Claims, 11 Drawing Sheets

FOREIGN PATENT DOCUMENTS

| WO | WO 93/00432 | 1/1993 |
| --- | --- | --- |
| WO | WO 93/04692 | 3/1993 |
| WO | WO 93/09229 | 5/1993 |
| WO | WO 98/51354 | 11/1998 |
| WO | WO 99/21574 | 5/1999 |
| WO | WO 00/21998 | 4/2000 |
| WO | WO 01/74379 | 10/2001 |

OTHER PUBLICATIONS

Border et al., 1994, New England Journal of Medicine 331:1286-1292.*

Asahina et al., "Human Osteogenic Protein-1 (hOP-1) Induces Chondroblastic Differentiation Of Osteoprogenitor Cells Derived From Newborn Rat Calvaria", *Bone and Mineral Research*, 7:S205 452 (1992).

Basler et al. Control of Cell Pattern in the Neural Tube: Regulation of Cell Differentiation by dorsalin-1, a Novel TGF-beta Family Member. Cell 73, 687-702 (1993).

Begue-Kim et al. Effects of Dentin Proteins, Transforming Growth Factor Beta1 and Bone Morphogenetic Protein 2 (BMP2) on the Differentiation of Odontoblast in vitro. Int. J. Dev. Biol. 36, 491-503 (1992).

Behringer et al. Abnormal Sexual Development in Transgenic Mice Chronically Expressing Mullerian Inhibiting Substance. Nature 345, 167-170 (1990).

Border, et al., "Suppression of experimental Glomerulonephritis by antiserum against transforming growth factor ∃1", *Nature*, 346:371-374 (1990).

Border, et al., "Transforming Growth Factor-∃ in Disease: The Dark Side of Tissue Repair", *J. Clin. Invest.*, 90:1-7 (1992).

Broxmeyer et al., "Human umbilical cord blood as a potential source of transplantable hematopietic stem/progenitor cells", *Proc. Natl. Acad. Sci.*, 86:3828-3832 (1989).

Castilla et al., Transforming Growth Factors ∃1 and ∀ in Chronic Liver Disease *New England Journal of Medicine*, 324:933-939 (1991).

Cate et al. Isolation of the Bovine and Human Genes for Mullerian Inhibiting Substance and Expression of the Human Gene in Animal Cells. Cell 45,685-698 (1986).

Celeste et al. "Highly Purified Bovine Bone-Inductive Activity Contains Multiple Protein Species Related to BMP-2", *Journal of Cellular Biochemistry*, 54:105 (1990).

Celeste et al. Identification of Transforming Growth Factor Beta Family Members Present in Bone-Inductive Protein Purified from Bovine Bone. PNAS 87, 9843-9847 (1990).

Celeste et al., "Molecular Cloning of BMP-8: A Protein Present in Bovine Bone Which is Highly Related to the BMP-5/6/7 Subfamily of Osteoinductive Molecules", *Journal of Cellular Biochemistry*, Suppl. 16F 100W502 (1992).

Cheifetz t al., "A Surface Component on GH3 Pituitary Cells That Recognizes Transforming Growth Factor-∃, Activin, and Inhibin", *Journal of Biological Ch mistry*, 263:17225-17228 (1988).

Chen et al. Bone Morphogenetic Protein-2b Stimulation of Growth and Osteogenic Phenotypes in Rat Osteoblast-like Cells: Comparison with TGF-Beta. J. Bone Min. Res. 6, 1387-1393 (1991).

Chomcyznski et al. Single-Step Method of RNA Isolation by Acid Guanidinium Thiocyanant-Phenol-Chloroform Extraction. Anal. Biochem. 162, 156-169 (1987).

Clark et al., "Coregulation of Collagenase and Collagenase Inhibitor Production by Phorbol Myristate Acetate in Human Skin Fibroblasts", *Arch. Bio. Chem. Biophys.*, 241:36-44 (1985).

Coffman et al., "Xotch, the Xenopus Homolog of Drosophila notch", *Science*, 249:1438-1441 (1990).

Dahlin et al. "Generation of New Bone Around Titanium Implants Using a Membrane Technique: An Experimental Study in Rabbits", *International Journal of Oral & Maxillofacial Implants*, 4:19-25 (1989).

D'Allesandro et al. Purification, Characterization and Activity of Recombinant Human BMP-5. J. Cell Biochem. Suppl. 166, Abstract No. Q105 (1991).

Dexter et al., "Growth and Differentiation on the Hemopoietic System", *Ann. Rev. Cell Biol.*, 3:423-441 (1987).

Fausto et al., "Effects of TGF- s in the liver: cell proliferation and fibrogenesis", *Ciba Found. Symp.*, 157:165-174 (1991).

Fitgerald et al. (1990), "Autoradiographic Analysis of Odontoblast Replacement Following Pupl Exposure In Primate Teeth," 35 *Archs. Oral Biol.* 9:707-715.

Fitzgerald et al. (1991), "A Clinical and Histological Evaluation of Conservative Pulpal Therapy in Human Teeth," 16 *Operative Dentistry* 101-112.

Forage et al., "Cloning and sequence analysis of cDNA species coding for the two subunits of inhibin from bovine follicular fluid", *Proc. Natl. Acad. Sci.*, 83:3091-3095 (1986).

George et al., "Current Methods in Sequence Comparison and Analysis", *Macromolecular Sequencing and Synthesis Selected Methods and Applications*, 127-149 (1988).

Gray et al., "Requirement for Activin A and Transforming Growth Factor- 1 Pro-Regions in Homodimer Assembly", *Science*, 247:1328-1330 (1990).

Green et al. Graded Changes in Dose of a Xenopus Activin A Homologue Elicit Stepwise Transitions in Embryonic Cell Fate. Nature 347, 391-394 (1990).

Hall et al., "Stem Cells: the generation and maintenance of cellular diversity", *Development*, 106:619-633 (1989).

Haskell et al. (1978), "Dir ct Pulp Capping Treatment: A Long-T rm Follow-Up," 97 *JADA* 607-612.

Heath et al., "Regulatory factors of embryonic stem cells", *J. Cell. Sci.*, Suppl. 10:257-266 (1988).

Heikinheimo (1994), "Stage-Specific Expression of Decapentaplegic-Vg-Related Genes 2, 4, and 6 (Bone Morphogenetic Proteins 2, 4, and 6) During Human Tooth Morphogenesis," 73 *J. Dent. Res.* 3:590-597.

Helder et al. (1995), "Expression Pattern of Osteogenic Protein-1 (Bone Morphogenetic Protein-7) in Human and Mouse Development," 43 *J. Histochem. Cytochem.* 10:1035-1044.

Israel et al., "Expression and Characterization of Bone Morphogenetic Protein-2 in Chinese Hamster Ovary Cells", *Growth Factors*, 7:139-150 (1992).

Israel et al., "Expression of Recombinant BMP2 in Chinese Hamster Ovary Cells", *Journal of Cellular Biochemistry*, p. 168, Q111 (1991).

Jepsen et al. (1995), "Regeneration of Mineralized Dental Tissues Induced by Recombinant Human Osteogenic Protein-1," 56 *Calc. Tiss. Intl.* 5:463.

Katagiri et al. The Non-Osteogenic Mouse Pluripotent Cell Line, C3H10T1/2 is Induced to Differentiate into Osteoblastic Cells by Recombinant Human Bore Morphogenetic Protein-2. Biochem. Biophys. Res. Comm. 172, 295-299 (1990).

Khalil et al., "Increased Production and Immunohistochemical Localization of Transforming Growth Factor- in Idiopathic Pulmonary Fibrosis", *American Journal of Respiratory Cell and Molecular Biology*, 5:155-162 (1991).

Kingsley. The TGF-Beta Superfamily: New Members, New Receptors, and New Genetic Tests of Function in Different Organisms. Genes Dev. 8, 133-146 (1994).

Krummel et al., "Transforming Growth Factor Beta (TGF- ) Induces Fibrosis in a Fetal Wound Model", *Journal of Pediatric Surgery*, 23:647-652 (1988).

Lee. Identification of a Novel Member (GDF-1) of the Transforming Growth Factor-Beta Superfamily. Mol. Endocrinol. 90, 1034-1040 (1990).

Lee. Expression of Growth/Differentiation Factor 1 in the Nervous System: Conversation of a Bicistronic Structure. PNAS 88, 4250-4254 (1991).

Lianjia et al. (1993), "Bovine Bone Morphogenetic Protein-Induced Dentinogenesis," 295 *Clin. Orthop. Rel. Res.* 305-312.

Lyons et al. Patterns of Expression of Murine Vgr-1 and BMP-2a RNA Suggest that Transforming Growth Factor-Beta-like Genes Coordinately Regulate Aspects of Embryonic Development. Genes and Development 3, 1657-1668 (1989).

Lyons et al. Vgr-1, a Mammalian Gen Relat d to Xenopus Vg-1, is a Member of the Transforming Growth Factor-Beta Gene Superfamily. PNAS 86, 4554-4558 (1989).

Malluche et al., "Renal bone disease 1990: An unmet challenge for the nephrologists" *Kidney Intern.*, 38:193-211 (1990).
Mankin, "Rickets, Osteomalacia, and Renal Osteodystrophy", *The Orthopedic Clinics of North America*, 21:81-96 (1990).
Mason et al. Complementary DNA Sequences of Ovarian Follicular Fluid Inhibin Show Precursor Structure and Homology with Transforming Growth Factor-Beta. Nature 318, 659-663 (1985).
Mason et al. Activin B: Precursor Sequences, Genomic Structure and in Vitro Activities. Mol. Endocrinol. 3, 1352-1358 (1989).
Massagué, "The TFG- Family of Growth and Differentiation Factors", *Cell*, 49:437-438 (1987).
Mitsiadis et al., "Midkine (MK), a Heparin-Binding Growth/Differentiation Factor, Is Regulated by Retinoic Acid and Epithelial-Mesenchymal Interactions in the Developing Mouse Tooth, and Affects Cell Proliferation and Morphogenesis", *J. Cell Biol.*, 129: (1995).
Miller et al. Phenotypic Modulation of the Swarm Rat Chondrosarcoma Induced by Morphogenetic Bone Matrix. Cancer Res. 42, 2589-2594 (1987).
Nakashima. Induction of Dentine in Amputated Pulp of Dogs by Recombinant Human Bone Morphogenetic Proteins-2 and -4 with Collagen Matrix. Archs. Oral Biol. 39, 1085-1089 (1994).
Nakashima, J. (1990), "The Induction Of Reparative Dentine In The Amputated Dental Pulp Of The Dog By Bone Morphogenetic Protein," 35 *Archs. Oral Biol.* 7:493-497.
Nakashima, J. (1990), "The Induction Of Reparative Dentine in the Amputated Dental Pulp of the Dog by Bone Morphogenetic Protein," *Archs oral boil*, 35:493-497 (1990).
Ngo et al. The Protein Folding Problem and Tertiary Structure Prediction. Merz et al., eds., Birkhauser, Boston, p. 492-495 (1994).
Okuda et al., "Elevated Expression of Transforming Growth Factor- and Proteoglycan Production in Experimental Glomerulonephritis", *J. Clin. Invest.*, 86:453-462 (1990).
Ozkanayak et al. OP-1 cDNA Encodes an Osteogenic Protein in the TGF-Beta Family. EMBO J. 9, 2085-20936 (1990).
Ozkaynet et al. Murine Osteogenic Protein-1 (OP-1), High levels of mRNA in Kidney. Biochem. Biophys. Res. Comm. 179, 116-123 (1991).
Padgett et al. A Transcript From a *Drosophila* Patt rn Gene Predicts a Prot in Homologous t the Transforming Growth Factor-Beta Family. Nature 325, 81-84 (1987).
Padgett et al. Human BMP Sequenc s can Conf r Normal Dorsal-Ventral Patterning in the *Drosophila* Embryo. PNAS 90, 2905-2909 (1993).
Padgett et al. "Human BMP sequences can confer normal dorsal-ventral patterning in the *Drosophila* embryo", *Proc. Natl. Acad. Sci*, 90:2905-2909 (1993).
Panganiban et al. Biochemical Characterization of the *Drosophila* dpp Protein, a Member of the Transforming Growth Factor-Beta Family of Growth Factors. Mol. Cell. Biol. 10, 2669-2677 (1990).
Pepinsky et al., "Proteolytic Processing of Mulerian Inhibiting Substance Produces a Transforming Growth Factor- -like Fragment", *Journal of Biological Chemistry*, 263:18961-18964 (1988).
Perides et al. Regulation of Neural Cell Adhesion Molecule and L1 by the Transforming Growth Factor-Beta Superfamily. J. Cell. Biol. 269, 765-770 (1994).
Posttethwaite et al., "Modulation of Fibroblast Functions by Interleukin 1: Increased Steady-State Accumulation of Type 1 Procollagen Messenger RNAs and Stimulation of Other Functions but Not Chemotaxis by Human Recombinant Interleukin 1 and ", *J. Cell Biol.*, 106:311-318 (1988).
Posttethwaite et al., "Stimulation of Glycosaminoglycan Synthesis in Cultered Human Dermal Fibroblasts by Interleukin 1", *J. Clin. Invest.*, 83:629-636 (1989).
Ritz et al., "Genesis of Bone Disease in Uremia", *Bone and Mineral Research*, 5:309-374 (1987).
Rogers et al. Bone Morphogenetic Proteins-2 and -4 are Involved in the Retinoic Acid-Induced Differentiation of Embryonal Carcinoma Cells. Mol. Biol. Cell 3, 189-196 (1992).
Rosen et al. Purification and Molecular Cloning of a Novel Group of BMPs and Localization of BMP mRNA in Developing Bone. Connect Tissue Res. 20, 313-319 (1989).
Rosen et al. "Development Expression of Cartilage and E-Specific Genes in the Rat Embryo", *Calcified Tissue*, 42 A35:136 (1988).
Rosen et al. In Vivo and In Vitro Roles of BMP in Skeletal Formation and Repair, *Journal of Cellular Biochemistry*, 33:004 (1990).
Rosen et al. "Isolation and Characterization of BMP-Responsive Cartilage and Bone, Cell Progenitors From Mouse Embryo Limb Buds", *Journal of Cellular Biochemistry*, Suppl. 16F 103:W513 (1992).
Rosenberg, "The Pathology of Metabolic Bone Disease", *Radiologic Clinics of North America*, 29:19-35 (1991).
Rutherford et al. (1995), "A New Biological Approach to Vital Pulp Therapy," 6 *Crit. Rev. Oral Biol. Med.* 3:218-229.
Sampath et al, Homology of Bone-Inductive Proteins from Human, Monkey, Bovine, and Rat Extracellular Matrix. PNAS 80, 6591-6595 (1983).
Sampath et al. Bovine Osteogenic Protein is Composed of Dimers of OP-1 and BMP-2A, Two Membersof the Transforming Growth Factor-Beta Superfamily. J. Biol. Chem. 265, 13198-13205 (1990).
Sampath et al. *Drosophila* Transforming Growth Factor Beta Superfamily Protein Induce Endochondral Bone Formation in Mammals. PNAS 90, 6004-6008 (1993).
Schubert et al. Activin is a Nerve Cell Survival Molecule. Nature 344, 868-870 (1990).
Schultz et al., "Neovascular Growth Factors", *Eye*, 5:170-180 (1991).
Smith et al. Identification of a Potent Xenopus Mesoderm-Inducing Factor as a Homologue of Activin A. Nature 345, 729-731 (1990).
Smith et al. (1990), "In Vivo Morphogenic Activity of Dentine Matrix Proteins," 18 *J. Biol. Buccale* 123-129.
Smith et al. (1990), "Preliminary Studies On The In Vivo Morphogenic Properties of Dentine Matrix Proteins," 11 *BioMaterials* 22-24.
Sokol et al. A Mouse Macrophage Factor Induces Head Structures and Organizes a Body Axis in Xenopus. Science 249, 561-563 (1990).
Storm et al. Limb Alterations in Brachypodism Mice Due to Mutations in a New Member of the TGF-Beta-Superfamily. Nature 368, 639-343 (1994).
Sugino et al., "Identification of a Specific Receptor for Erythroid Differentiation Factor on Follicular Granulosa Cell", *Journal of Biological Chemistry*, 263:15249-15252 (1988).
Suwa et al. Inductive Effect on Bovine Bone Morphogenetic Protein on Human Dental Pulp Tissue in vitro. J. Med. Coll. PLA (9)2, 108-111 (1994).
Takuwa et al. Bone Morphogenetic Protein-2 Stimulates Alkaline Phosphatase Activity and Collagen Synthesis in Cultured Osteoblastic Cells, MC3T3-E1. Biochem. Biophys. Res. Comm. 174, 96-101 (1991).
Thesleff et al. (1995), "Regulation of organogenesis. Common molecular mechanisms regulating the development of teeth and other organs," 39 *Int. J. Dev. Biol.* 35-50.
Thies et al. Recombinant Human Bone Morphogenetic Protein-2 Induces Osteoblastic Differentiation in W-20-17 Stormal Cells. Endocrinol. 130, 1318-1324 (1992).
Tureckova et al. (1995), "Comparison of expression of the msx-1, msx-2, BMP-2 and BMP-4 genes in the mouse upper diastemal and molar tooth primordial," 39 *Int. J. Dev. Biol.* 459-468.
Tzamaloukas, "Diagnosis and Management of Bon Disorder in Chronic Renal Failur and Dialyzed Patients", *Medical Clinics of North America*, 74:961-974 (1990).
Vaahtokari et al. (1996), "The enamel knot as a signaling center in the developing mouse tooth," 54 *Mechanisms of Development* 39-43.
Vainio et al. (1993), "Identification of BMP-4 as a Signal Mediating Secondary Induction Between Epithelial and Mesenchymal Tissues During Early Tooth Development," 75 *Cell* 45-58.
Vale et al., "Purification and characterization of an FSH releasing protein from porcine ovarian follicular fluid", *Nature*, 321:776-782 (1986).
Van den Eijnden-Van Raaij et al., "Activin-like factor from a *Xenopus laevis* cell line responsible for mesoderm induction", *Nature*, 345:732-734 (1990).

Vukicevic et al., "Localization of Osteogenic Protein-1 (Bone Morphogenic Protein-7) During Human Embryonic Development: High Affinity Binding to Basement Membranes", *Biochemical and Biophysical Research Communications*, 198:693-700 (1994).

Vukicevic et al., "Osteogenin Inhibits Proliferation and stimulates Differentiation In Mouse Osteoblast-Like Cells (MC3T3-E1)", *Biochem. Biophys. Res. Comm.*, 166:750-756 (1990).

Vikicevic et al., "Stimulation of the expression of osteogenenic and chondrogenic phenotypes in vitro by osteogenin", PNAS, 86:8793-8797 (1989).

Wang et al. Purification and Characterization of Other Distinct Bone-Inducing Proteins. PNAS 85, 9484-9488 (1988).

Wang et al. "Purification and Characteristics of Cartilgage and Bone Inducing Factors", *Calcified Tissue*, 42 A37:146 (1988).

Wang et al. Recombinant Human Bone Morphogenetic Protein Induces Bone Formation. PNAS 87, 2220-2224 (1990).

Weeks et al. A Maternal mRNA Localized to the Vegetal Hemisphere in Xenopus Eggs Codes for a Growth Factor Related TGF-Beta. Cell 51, 861-867 (1987).

Wells. Biochemistry 29, 8509-8517 (1990).

Wharton et al. *Drosophila* 60A Gene, Another Transforming Growth Factor Beta Family Member, is Closely Related to Human Bone Morphogenetic Proteins. PNAS 88, 9214-9218 (1991).

Whitby et al., "Immunohistochemical Localization of Growth Factors in Fetal Wound Healing", *Developmental Biology*, 147:207-215 (1991).

Williams, "The role of diffusible molecules in regulating the cellular differentiation of *Dictyostelium discoideum*", *Development*, 103:1-16 (1988).

Wong et al., "Target c lls in b n for parathormone and calcitonin are differ nt: Entrichment for each cell type by sequential digestion of mouse calvaria and selective adhesion to polymeric surfaces", *PNAS*, 72:3167-3171 (1975).

Wozney et al. Novel Regulators of Bone Formation: Molecular Clones and Activities. Science 242, 1528-1534 (1988).

Wozney. Bone Morphogenic Proteins. Prog. Growth Factor Res. 1, 267-280 (1990).

Wozney et al. Growth Factors Influencing Bone Development. J. Cell Sci. Suppl. 13, 149-156 (1990).

Wozney et al. The Bone Morphogenetic Family and Osteogenesis. Mol. Reprod. Dev. 32, 160-167 (1992).

Wozney et al., "Regulation of Chondrogenesis and Osteogenesis by the BMP Proteins," *Journal of Cellular Biochemistry*, Suppl. 16F 76:W026 (1992).

Wozney et al., "Identification Through Molecular Clong of Factors Involved in In Vivo Cartilage Formation", *Calcium Tissue*, 42 A37:146 (1988).

Yamaguchi et al. Recombinant Human Bone Morphogenetic Protein-2 Stimulates Osteoblastic Maturation and Inhibits Myogenic Differentiation in Vitro. J. Cell Biol. 113, 681-687 (1991).

Yannas, Biologically Active Analogues of the Extracellular Matrix: Artificial Skin and Nerves. Angew. Chem. Int. Ed. Engl. 29, 20-35 (1990).

Nakashima, M., "Dentin induction by implants of autolyzed antigen-extracted allogeneic dentin on amputated pulps of dogs", Endod Dent Traumatol 1989; 5; 279-286.

Lyons et al., Organogenesis and pattern formation in the mouse: RNA distribution patterns suggest a role for *Bone Morphogenetic Protein-2A (BMP-2A)* Development 109, 833-844, 1990.

Jones et al., "Involvement of *Bone Morphogenetic Protein-4* (BMP-4) and *Vgr-1* in morphogenesis and neurogenesis in the mouse", Development 111, 531-542, 1991.

Vale et al., "The Inhibin/Activin Family of Hormones and Growth Factors", Handbook of Experimental Pharmacology 95, Chapter 26, p. 211-248, 1990.

Kawai and Urist, "Bovine Tooth -derived Bone Morphogenetic Protein", J. Dent Res 68(6): 1069-1074, 1989.

Olson, L., "Grafts and Growth Factors in CNS" Proceedings of the Xth Meeting of the World Society for Stereotactic and Functional Neurosurgery, Maebashi, Japan, Oct. 1989, Stereotact Funct Neurosurg 1990; 54-55; 250-267.

Merrill and Zimmerman, "Natural and Induced Cytotoxicity of Oligodendrocytes by Microglia is inhibitable by TGFβ", GLIA 4:327-331, 1991.

Martinou et al., "Transforming growth factor $\beta_1$ is a potent survival factor for rat embryo motoneurons in culture", Developmental Brain Research, 52 (1990) 175-181.

The Wall Street Journal, "Research Group Identifies Factors That Are Linked to Bone Growth", Friday, Dec. 16, 1988.

Applied Genetic News, vol. 9, No. 6, Jan. 1989.

Takao et al., "Identification of Rat Bone Morphogenetic Protein-3b (BMP-3b), a New Member of BMP-3", Biochemical and Biophysical Research Communications 219, p. 656-662 (1996).

Daluiski et al., "Bone morphogenetic protein-3 is a negative regulator of bone density", Nature Genetics, vol. 27, Jan. 2001, p. 84-88.

Weber et al., "Evidence for the Upregulation of Osteogenic Protein-1 mRNA Expressin in Musculosketal Neoplasms", Journal of Orthopedic Research, 16:8-14, 1998.

Kleeff et al., "Bone Morphogenetic Protein 2 Exerts Diverse Effects on Cell Growth In Vitro and Is Expressed in Human Pancrfeatic Cancer In Vivo", Gastroenterology 1999; 116:1202-1216.

Bentley et al., "Expression of bone morphogenetic proteins in human prostatic adenocarcinoma and benign prostatic hyperplasia", Br. J. Cancer (1992), 66, 1159-1163.

Autzen et al., "Bone morphogenetic protein 6 in skeletal metastases from prostate cancer and other common human malignancies", British Journal of Cancer (1998), 78(9), 1219-1223.

Stelnicki et al., "Bone Morphogenetic Protein-2 Induces Scar Formation and Skin Maturation in the Second Trimester Fetus", Plastic and Reconstructive Surgery, Jan. 1998, p. 12-19.

Detmer and Walker, "Bone Morphogenetic Proteins Act Synergistically With Haematopoietic Cytokines In The Differentiation of Haematopoietic Progenitors", Cytokine, vol. 17, No. 1, 2002: p. 36-42.

Gratacos et al., "Bone morphogenetic protein-2, but not bone morphogenetic protein-7, promotes dendritic growth and calbindin phenotype in cultured rat strial neurons", Neuroscience 2001, 104(3):783-90 (Abstract only).

Dayhoff, Atlas of Protein Sequence and Structure, vol. 5, Supplement 3, 345-363, 1978.

Hogan, B., "Bone morphogenetic proteins: multifunctional regulators of vertebrate development", Genes & Development 10:1580-1594 (1996).

Marker et al., "Spectrum of *Bmp5* Mutations From Germline Mutagenesis Experiments in Mice", Genetics 145 (1997) 435-443.

Schwabe et al., "Brachydactyly Type C Caused by a Homozygous Missense Mutation in the Prodomain of CDMP1", American Journal of Medical Genetics 124A:356-363 (2004).

Everman et al., "The Mutational Spectrum of Brachydactyly Type C", American Journal of Medical Genetics 112:291-298 (2002).

Griffith et al., Three-dimensional structure of recombinant human osteogenic protein 1: Structural paradigm for the transforming growth factor β superfamily, Proc. Natl. Acad. Sci. USA, vol. 93, 878-883, Jan. 1996.

\* cited by examiner

PROTEIN-INDUCED MORPHOGENESIS OF KIDNEY TISSUE

REFERENCE TO RELATED APPLICATIONS

The present application is a continuation of U.S. Ser. No. 09/464,206, filed on Dec. 15, 1999, to be issued as U.S. Pat. No. 6,531,445; which is a division of U.S. Ser. No. 08/396,684, filed on Mar. 1, 1995, now abandoned; which is a continuation of U.S. Ser. No. 08/091,395, filed Jul. 13, 1993, now abandoned; which is a continuation of U.S. Ser. No. 07/752,764, filed Aug. 30, 1991, now abandoned; which is a continuation-in-part of U.S. Ser. No. 07/ 667,274, filed on Mar. 11, 1991, now abandoned. The entire contents of the above-mentioned applications are incorporated by reference herein.

BACKGROUND OF THE INVENTION

This invention relates to morphogenic proteins which can induce tissue morphogenesis in mammals; to methods of identifying these proteins and obtaining them from natural sources or producing synthetic forms of these proteins by expressing recombinant DNA encoding the proteins; to the fabrication of tissue-specific acellular matrices; and to methods for promoting tissue stasis, repair and regeneration, and methods for increasing progenitor cell populations using these proteins.

Cell differentiation is the central characteristic of morphogenesis which initiates in the embryo, and continues to various degrees throughout the life of an organism in adult tissue repair and regeneration mechanisms. The degree of morphogenesis in adult tissue varies among different tissues and is related, among other things, to the degree of cell turnover in a given tissue. On this basis, tissues can be divided into three broad categories: (1) tissues with static cell populations such as nerve and skeletal muscle where there is no cell division and most of the cells formed during early development persist throughout adult life; (2) tissues containing conditionally renewing populations such as liver where there is generally little cell division but, in response to an appropriate stimulus, cells can divide to produce daughters of the same differentially defined type; and (3) tissues with permanently renewing populations including blood, testes and stratified squamous epithelia which are characterized by rapid and continuous cell turnover in the adult. Here, the terminally differentiated cells have a relatively short life span and are replaced through proliferation of a distinct subpopulation of cells, known as stem or progenitor cells.

The cellular and molecular events which govern the stimulus for differentiation of these cells is an area of intensive research. In the medical field, it is anticipated that the discovery of factor(s) which control cell differentiation and tissue morphogenesis will significantly advance medicine's ability to repair and regenerate diseased or damaged mammalian tissues and organs. Particularly useful areas include reconstructive surgery and in the treatment of tissue degenerative diseases including arthritis, emphysema, osteoporosis, cardiomyopathy, cirrhosis, and degenerative nerve diseases.

A number of different factors have been isolated in recent years which appear to play a role in cell differentiation. Some of these factors are gene transcription activators such as the NOTCH gene, identified in *Drosophila* and the related XOTCH gene identified in *Xenopus*, as well as a number of transcription activators identified in *Caenorhabditis elegans*.

The hemopoietic system, because of its continually renewing cell population, is an area of concentrated study. Factors identified in this system which may be involved in cell renewal include interleukin 3 (IL-3), erythropoietin, the CSFs (GM-CSF, G-CSF, M-CSF et al.) and various stem cell growth factors.

Other proteins thought to play a role in cell differentiation include proteins that are members of the family of insulin-like growth factors (IGF), members of the family of heparin-binding growth factors, (e.g., FGF—acidic and basic fibroblast growth factors, and ECDGF—embryonal carcinoma-derived growth factor) as well as several transforming oncogenes (hst and int-2, see for example, Heath et al., (1988), *J. Cell Sci. Suppl.* 10:256–256.) DIF (Differentiation Inducing Factor), identified in *Dictyostelium discoideum*, is another bioregulatory protein, directing prestock cell differentiation in that organism.

The structurally related proteins of the TGF-β superfamily of proteins also have been identified as involved in a variety of developmental events. For example, TGF-β and the polypeptides of the inhibin/activin group appear to play a role in the regulation of cell growth and differentiation. MIS (Mullerian Inhibiting Substance) causes regression of the Mullerian duct in development of the mammalian male embryo, and DPP, the gene product of the *Drosophila decapentaplegic* complex is required for appropriate dorsal-ventral specification. Similarly, Vg-1 is involved in mesoderm induction in *Xenopus*, and Vgr-1 has been identified in a variety of developing murine tissues.

Another source that has revealed a wealth of information is in the area of bone morphogenesis. The development and study of a bone model system has identified the developmental cascade of bone differentiation as consisting of chemotaxis of mesenchymal cells, proliferation of these progenitor cells, differentiation of these cells into of cartilage, vascular invasion, bone formation, remodeling, and finally, marrow differentiation (Reddi (1981) Collagen Rel. Res. 1:209–206). Proteins capable of inducing endochondral bone formation in a mammal when implanted in association with a matrix now have been identified in a number of different mammalian species, as have the genes encoding these proteins, (see, for example, U.S. Pat. No. 4,968,590; U.S. Ser. No. 315,342 filed Feb. 23, 1989; and U.S. Ser. No. 599,543, filed Oct. 18, 1990). These proteins, which share significant amino acid sequence homology with one another as well as structural similarities with various members of the TGF-β super family of proteins, have been shown to induce endochondral bone formation and/or bone cartilage formation when implanted in a mammal in association with a suitably modified matrix. Proteins capable of inducing a similar developmental cascade of tissue morphogenesis of other tissues have not been identified.

It is an object of this invention to provide morphogenic proteins ("morphogens"), and methods for identifying these proteins, which are capable of inducing the developmental cascade of tissue morphogenesis for a variety of tissues in mammals different from bone or bone cartilage. This morphogenic activity includes the ability to induce proliferation and differentiation of progenitor cells, and the ability to support and maintain the differentiated phenotype through the progression of events that results in the formation of adult tissue. Another object is to provide genes encoding these proteins as well as methods for the expression and isolation of these proteins, from either natural sources or biosynthetic sources, using recombinant DNA techniques. Still another object is to provide tissue-specific acellular matrices that may be used in combination with these proteins, and methods for their production. Other objects include providing methods for increasing a progenitor cell population in a mammal, methods for stimulating progenitor cells to differentiate in vivo or in vitro and maintain their differentiated phenotype, methods for inducing tissue-specific growth in vivo and methods for the replacement of diseased or damaged tissue in vivo. These and other objects and features of the invention will be apparent from the description, drawings, and claims which follow.

SUMMARY OF THE INVENTION

This invention provides morphogenic proteins ("morphogens") capable of inducing the developmental cascade of tissue morphogenesis in a mammal. In particular, these proteins are capable of inducing the proliferation of uncommitted progenitor cells, and inducing the differentiation of these stimulated progenitor cells in a tissue-specific manner under appropriate environmental conditions. In addition, the morphogens are capable of supporting the growth and maintenance of these differentiated cells. These morphogenic activities allow the proteins of this invention to initiate and maintain the developmental cascade of tissue morphogenesis in an appropriate, morphogenically permissive environment, stimulating stem cells to proliferate and differentiate in a tissue-specific manner, and inducing the progression of events that culminate in new tissue formation. These morphogenic activities also allow the proteins to stimulate the "redifferentiation" of cells previously induced to stray from their differentiation path. Under appropriate environmental conditions it is anticipated that these morphogens also may stimulate the "dedifferentiation" of committed cells (see infra.)

In one aspect of the invention, the proteins and compositions of this invention are useful in the replacement of diseased or damaged tissue in a mammal, particularly when the damaged tissue interferes with normal tissue or organ function. Accordingly, it is anticipated that the proteins of this invention will be useful in the repair of damaged tissue such as, for example, damaged lung tissue resulting from emphysema, cirrhotic kidney or liver tissue, damaged heart or blood vessel tissue, as may result from cardiomyopathies and/or atherothrombotic or cardioembolic strokes, damaged stomach tissue resulting from ulceric perforations or their repair, damaged neural tissue as may result from physical injury, degenerative diseases such as Alzheimer's disease or multiple sclerosis or strokes, damaged dentin tissue as may result from disease or mechanical injury, and damaged cartilage and ligament tissue. When the proteins of this invention are provided to, or their expression stimulated at, a tissue-specific locus, the developmental cascade of tissue morphogenesis is induced (see infra). Cells stimulated ex vivo by contact with the proteins or agents capable of stimulating morphogen expression in these cells also may be provided to the tissue locus. In these cases the existing tissue provides the necessary matrix requirements, providing a suitable substratum for the proliferating and differentiating cells in a morphogenically permissive environment, as well as providing the necessary signals for directing the tissue-specificity of the developing tissue. Alternatively, the proteins or stimulated cells may be combined with a formulated matrix and implanted as a device at a locus in vivo. The formulated matrix should be a biocompatible, preferably biodegradable, appropriately modified tissue-specific acellular matrix having the characteristics described below.

In many instances, the loss of tissue function results from scar tissue, formed in response to an initial or repeated injury to the tissue. The degree of scar tissue formation generally depends on the regenerative properties of the injured tissue, and on the degree and type of injury. Thus, in another aspect, the invention includes morphogens that may be used to prevent or substantially inhibit the formation of scar tissue by providing the morphogens, or morphogen-stimulated cells, to a newly injured tissue loci (see infra).

The morphogens of this invention also may be used to increase or regenerate a progenitor or stem cell population in a mammal. For example, progenitor cells may be isolated from an individual's bone marrow, stimulated ex vivo for a time and at a morphogen concentration sufficient to induce the cells to proliferate, and returned to the bone marrow. Other sources of progenitor cells that may be suitable include biocompatible cells obtained from a cultured cell line, stimulated in culture, and subsequently provided to the body. Alternatively, the morphogen may be provided systemically, or implanted, injected or otherwise provided to a progenitor cell population in an individual to induce its mitogenic activity in vivo. For example, an agent capable of stimulating morphogen expression in the progenitor cell population of interest may be provided to the cells in vivo, for example systemically, to induce mitogenic activity. Similarly, a particular population of hemopoietic stem cells may be increased by the morphogens of this invention, for example by perfusing an individual's blood to extract the cells of interest, stimulating these cells ex vivo, and returning the stimulated cells to the blood. It is anticipated that the ability to augment an individual's progenitor cell population will significantly enhance existing methods for treating disorders resulting from a loss or reduction of a renewable cell population. Two particularly significant applications include the treatment of blood disorders and impairment or loss of immune function. Other cell populations whose proliferation may be exploited include the stem cells of the epidermis, which may be used in skin tissue regeneration, and the stem cells of the gastrointestinal lining for healing of ulcers.

In still another aspect of the invention, the morphogens also may be used to support the growth and maintenance of differentiated cells, inducing existing differentiated cells to continue expressing their phenotype. It is anticipated that this activity will be particularly useful in the treatment of tissue disorders where loss of function is caused by cells becoming senescent or quiescent, such as may occur in osteoporosis. Application of the protein directly to the cells to be treated, or providing it by systemic injection, can be used to stimulate these cells to continue expressing their phenotype, thereby significantly reversing the effects of the dysfunction (see infra). Alternatively, administration of an agent capable of stimulating morphogen expression in vivo also may be used. In addition, the morphogens of this invention also may be used in gene therapy protocols to stimulate the growth of quiescent cells, thereby potentially enhancing the ability of these cells to incorporate exogenous DNA.

In yet another aspect of the invention, the morphogens of this invention also may be used to induce "redifferentiation" of cells that have strayed from their differentiation pathway, such as can occur during tumorgenesis. It is anticipated that this activity of the proteins will be particularly useful in treatments to reduce or substantially inhibit the growth of neoplasms. The method also is anticipated to induce the de-and re-differentiation of these cells. As described supra, the proteins may be provided to the cells directly or systemically, or an agent capable of stimulating morphogen expression in vivo may be provided.

Finally, modulations of endogenous morphogen levels may be monitored as part of a method for detecting tissue dysfunction. Specifically, modulations in endogenous morphogen levels are anticipated to reflect changes in tissue or organ stasis, and can be followed by monitoring fluctuations in the body's natural antibody titer to morphogens.

The morphogenic proteins and compositions of this invention can be isolated from a variety of naturally-occurring sources, or they may be constructed biosynthetically using conventional recombinant DNA technology. Similarly, the matrices may be derived from organ-specific tissue, or they may be formulated synthetically, as described below.

A key to these developments was the discovery and characterization of naturally-occurring osteogenic proteins followed by observation of their remarkable properties. These proteins, originally isolated from bone, are capable of inducing the full developmental cascade of bone formation, including vascularization, mineralization, and bone marrow differentiation, when implanted in a mammalian body in association with a suitably modified matrix. Native proteins capable of inducing this developmental cascade, as well as DNA sequences encoding these proteins now have been isolated and characterized for a number of different species (e.g., OP-1, OP-2, and CBMP-2. See, for example, U.S. Pat. Nos. 4,968,590 and 5,011,691; U.S. application Ser. No. 422,699, filed Oct. 17, 1989; and U.S. Ser. No. 600,024 and 599,543, both filed Oct. 18, 1990; Sampath et al. (1990) *J. Bio. Chem* 265:13198–13205 and Ozkaynak, et al. (1990) *EMBO* 9:2085–2093). The mature forms of these proteins share substantial amino acid sequence homology, especially in the C-terminal regions of the mature proteins. In particular, the proteins share a conserved six or seven cysteine skeleton in this region (e.g., the linear arrangement of these C-terminal cysteine residues is essentially conserved in the different proteins, in addition to other, apparently required amino acids (see Table II, infra).

Polypeptide chains not normally associated with bone or bone formation, but sharing substantial amino acid sequence homology with the C-terminus of the osteogenic proteins, including the conserved six or seven cysteine skeleton, also have been identified as competent for inducing bone in mammals. Among these are amino acid sequences identified in *Drosophila* and *Xenopus*, (e.g., DPP and Vg1; see, for example, U.S. Pat. No. 5,011,691 and Table II, infra). In addition, non-native biosynthetic constructs designed based on extrapolation from these sequence homologies, including the conserved six or seven cysteine skeleton, have been shown to induce endochondral bone formation in mammals when implanted in association with an appropriate matrix (See Table III, infra).

It has now been discovered that this "family" of proteins sharing substantial amino acid sequence homology and the conserved six or seven cysteine skeleton are true morphogens, capable of inducing, in addition to bone and bone cartilage, tissue-specific morphogenesis for a variety of other organs and tissues. The proteins apparently bind to surface receptors or otherwise contact and interact with progenitor cells, predisposing or stimulating the cells to proliferate and differentiate in a morphogenically permissive environment. The morphogens are capable of inducing the developmental cascade of cellular and molecular events that culminate in the formation of new organ-specific tissue, including any vascularization, connective tissue formation, and nerve ennervation as required by the naturally occurring tissue.

It also has been discovered that the way in which the cells differentiate, whether, for example, they differentiate into bone-producing osteoblasts, hemopoietic cells, or liver cells, depends on the nature of their local environment (see infra). Thus, in addition to requiring a suitable substratum on which to anchor, the proliferating and differentiating cells also require appropriate signals to direct their tissue-specificity. These signals may take the form of cell surface markers. Thus, in a suitable, typically bone powder-derived matrix presented in a vascular supported environment, the morphogen-activated progenitor cells differentiate not only through the bone-producing cascade including transformation to chondrocytes and then to osteoblasts, including formation of the necessary associated vascular network.

When the morphogens (or progenitor cells stimulated by these morphogens) are provided at a tissue-specific locus (e.g., by systemic injection or by implantation or injection at a tissue-specific locus, or by administration of an agent capable of stimulating morphogen expression in vivo), the existing tissue at that locus, whether diseased or damaged, has the capacity of acting as a suitable matrix. Alternatively, a formulated matrix may be externally provided together with the stimulated progenitor cells or morphogen, as may be necessary when the extent of injury sustained by the damaged tissue is large. The matrix should be a biocompatible, suitably modified acellular matrix having dimensions such that it allows the influx, differentiation, and proliferation of migratory progenitor cells, and is capable of providing a morphogenically permissive environment (see infra). The matrix preferably is tissue-specific, and biodegradable.

Formulated matrices may be generated from dehydrated organ-specific tissue, prepared for example, by treating the tissue with solvents to substantially remove the non-structural components from the tissue. Alternatively, the matrix may be formulated synthetically using a biocompatible, preferably in vivo biodegradable, structural polymer such as collagen in association with suitable tissue-specific cell attachment factors. Currently preferred structural polymers comprise tissue-specific collagens. Currently preferred cell attachment factors include glycosaminoglycans and proteoglycans. The matrix further may be treated with an agent or agents to increase the number of pores and micropits on its surfaces, so as to enhance the influx, proliferation and differentiation of migratory progenitor cells from the body of the mammal.

Among the proteins useful in this invention are proteins originally identified as osteogenic proteins, such as the OP-1, OP-2 and CBMP2 proteins, as well as amino acid sequence related proteins such as DPP (from *Drosophila*), Vg1 (from *Xenopus*), Vgr-1 (from mouse, see Table II and Seq. ID Nos.5–14), and the recently identified GDF-1 protein (Seq. ID No. 14). The members of this family, which include members of the TGF-β super-family of proteins, share substantial amino acid sequence homology in their C-terminal regions. Table I, below, describes the various morphogens identified to date, including their nomenclature as used herein, and Seq. ID references.

TABLE I

| | |
|---|---|
| "OP-1" | refers generically to the group of active proteins expressed from part or all of a DNA sequence encoding OP-1 protein, e.g., human OP-1 ("hOP-1", Seq. ID No. 5, mature protein amino acid sequence), or mouse OP-1 ("mOP-1", Seq. ID No. 6, mature protein amino acid sequence.) The conserved seven cysteine skeleton is defined by residues 38 to 139 of Seq. ID Nos. 5 and 6. |

TABLE I-continued

| | |
|---|---|
| "OP-2" | refers generically to the group of active proteins expressed from part or all of a DNA sequence encoding OP-2 protein, e.g., human OP-2 ("hOP-2", Seq. ID No. 7, mature protein amino acid sequence) or mouse OP-2 ("mOP-2", Seq. ID No. 8, mature protein amino acid sequence). The conserved seven cysteine sekelton is defined by residues 38 to 139 of Seq. ID Nos. 7 and 8. |
| "CBMP2" | refers generically to the active proteins expressed from a DNA sequence encoding CBMP2 protein, e.g., human CBMP2 ("CBMP2B(fx)", Seq ID No. 9) or bovine CBMP2 DNA ("CBMP2A(fx)", Seq. ID No. 10). |
| "Vgl(fx)" | refers to protein sequences encoded by the xenopus Vgl gene and defining the conserved seven cysteine skeleton (Seq. ID No. 11). |
| "Vgr-1(fx)" | refers to protein sequences encoded by the murine Vgr-1 gene and defining the conserved seven cysteine skeleton (Seq. ID No. 12). |
| "DPP(fx)" | refers to protein sequences encoded by the Drosophila DPP gene and defining the conserved seven cysteine skeleton (seq. ID No. 13). |
| "GDF-1(fx)" | refers to protein sequences encoded by the human GDF-1 gene and defining the conserved seven cysteine skeleton (seq. ID No. 14). |

The OP-2 proteins have an additional cysteine residue in this region (position 41), in addition to the conserved cysteine skeleton in common with the other proteins in this family. The GDF-1 protein has a four amino acid insert within the conserved skeleton (residues 44–47 of Seq. ID No. 14) but this insert likely does not interfere with the relationship of the cysteines in the folded structure. In addition, the CBMP2 proteins are missing one amino acid residue within the cysteine skeleton.

The morphogens are inactive when reduced, but are active as oxidized homodimers and as various oxidized heterodimers. Thus, as defined herein, a morphogen of this invention is a dimeric protein comprising a pair of polypeptide chains, wherein each polypeptide chain comprises at least the C-terminal six cysteine skeleton defined by residues 43–139 of Seq. ID No. 5, including functionally equivalent arrangements of these cysteines (e.g., amino acid insertions or deletions which alter the linear arrangement of the cysteines in the sequence but not their relationship in the folded structure), such that, when the polypeptide chains are folded, the dimeric protein species comprising the pair of polypeptide chains has the appropriate three-dimensional structure, including the appropriate intra- or inter-chain disulfide bonds such that the protein is capable of acting as a morphogen as defined herein. Specifically, the protein is capable of any of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of these cells. In addition, it is also anticipated that the morphogens of this invention will be capable of inducing dedifferentiation of committed cells under appropriate environmental conditions.

In one preferred aspect, the morphogens of this invention comprise one of two species of generic amino acid sequences: Generic Sequence 1 (Seq. ID No. 1) or Generic Sequence 2 (Seq. ID No. 2); where each Xaa indicates one of the 20 naturally-occurring L-isomer, α-amino acids or a derivative thereof. Generic Sequence 1 comprises the conserved six cysteine skeleton and Generic Sequence 2 comprises the conserved six cysteine skeleton plus the additional cysteine identified in OP-2. In another preferred aspect, these sequences further comprise the following sequence at their N-terminus:

```
Cys Xaa Xaa Xaa Xaa
 1               5
```

Preferred amino acid sequences within the foregoing generic sequences include: Generic Sequence 3 (Seq. ID No. 3) and Generic Sequence 4 (Seq. ID No. 4), listed below, which accommodate the homologies shared among the various members of this morphogen family identified to date, as well as the amino acid sequence variation among them. Note that these generic sequences allow for an additional cysteine at position 41 or 46 in Generic Sequences 3 or 4, respectively, providing an appropriate cysteine skeleton where inter-or intramolecular disulfide bonds can form, and contain certain critical amino acids which influence the tertiary structure of the proteins.

```
              Generic Sequence 3

Leu Tyr Val Xaa Phe
     1           5

Xaa Xaa Xaa Gly Trp Xaa Xaa Trp Xaa
                 10

Xaa Ala Pro Gly Xaa Xaa Xaa Ala
     15                  20

Xaa Tyr Cys Xaa Gly Xaa Cys Xaa
             25              30

Xaa Pro Xaa Xaa Xaa Xaa Xaa
                     35

Xaa Xaa Xaa Asn His Ala Xaa Xaa
             40              45

Xaa Xaa Leu Xaa Xaa Xaa Xaa Xaa
                     50

Xaa Xaa Xaa Xaa Xaa Xaa Xaa Cys
         55                      60

Cys Xaa Pro Xaa Xaa Xaa Xaa Xaa
                     65

Xaa Xaa Xaa Leu Xaa Xaa Xaa
     70                  75

Xaa Xaa Xaa Xaa Val Xaa Leu Xaa
                     80

Xaa Xaa Xaa Xaa Met Xaa Val Xaa
     85                      90

Xaa Cys Gly Cys Xaa
             95
``` wherein each Xaa is independently selected from a group of one or more specified amino acids defined as follows: "Res." means "residue" and Xaa at res.4=(Ser, Arg, Asp or Glu); Xaa at res.6=(Arg, Gln, Ser or Lys); Xaa at res.7=(Asp or Glu); Xaa at res.8=(Leu or Val); Xaa at res.11=(Gln, Leu, Asp, His or Asn); Xaa at res.12=(Asp, Arg or Asn); Xaa at res.14=(Ile or Val); Xaa at res.15=(Ile or Val); Xaa at res.18=(Glu, Gln, Leu, Lys, Pro or Arg); Xaa at res.20=(Tyr or Phe); Xaa at res.21=(Ala, Ser, Asp, Met, His, Leu or Gln); Xaa at res.23=(Tyr, Asn or Phe); Xaa at res.26=(Glu, His, Tyr, Asp or Gln); Xaa at res.28=(Glu, Lys, Asp or Gln); Xaa at res.30=(Ala, Ser, Pro or Gln); Xaa at res.31=(Phe, Leu or Tyr); Xaa at res.33=(Leu or Val); Xaa at res.34=(Asn, Asp, Ala or Thr); Xaa at res.35=(Ser, Asp, Glu, Leu or Ala); Xaa at res.36=(Tyr, Cys, His, Ser or Ile); Xaa at res.37=(Met, Phe, Gly or Leu); Xaa at res.38=(Asn or Ser); Xaa at res.39=(Ala, Ser or Gly); Xaa at res.40=(Thr, Leu or Ser); Xaa at res.44=(Ile or Val); Xaa at res.45=(Val or Leu); Xaa at res.46=(Gln or Arg); Xaa at res.47=(Thr, Ala or Ser); Xaa at res.49=(Val or Met); Xaa at res.50=(His or Asn); Xaa at res.51=(Phe, Leu, Asn, Ser, Ala or Val); Xaa at res.52=(Ile, Met, Asn, Ala or Val); Xaa at res.53=(Asn, Lys, Ala or Glu); Xaa at res.54=(Pro or Ser); Xaa at res.55=(Glu, Asp, Asn, or Gly); Xaa at res.56=(Thr, Ala, Val, Lys, Asp, Tyr, Ser or Ala); Xaa at res.57=(Val, Ala or Ile); Xaa at res.58=(Pro or Asp); Xaa at res.59=(Lys or Leu); Xaa at res.60=(Pro or Ala); Xaa at res.63=(Ala or Val); Xaa at res.65=(Thr or Ala); Xaa at res.66=(Gln, Lys, Arg or Glu); Xaa at res.67=(Leu, Met or Val); Xaa at res.68=(Asn, Ser or Asp); Xaa at res.69=(Ala, Pro or Ser); Xaa at res.70=(Ile, Thr or Val); Xaa at res.71=(Ser or Ala); Xaa at res.72=(Val or Met); Xaa at res.74=(Tyr or Phe); Xaa at res.75=(Phe, Tyr or Leu); Xaa at res.76=(Asp or Asn); Xaa at res.77=(Asp, Glu, Asn or Ser); Xaa at res.78=(Ser, Gln, Asn or Tyr); Xaa at res.79=(Ser, Asn, Asp or Glu); Xaa at res.80=(Asn, Thr or Lys); Xaa at res.82=(Ile or Val); Xaa at res.84=(Lys or Arg); Xaa at res.85=(Lys, Asn, Gln or His); Xaa at res.86=(Tyr, Ala or His); Xaa at res.87=(Arg, Gln or Glu); Xaa at res.88=(Asn, Glu or Asp); Xaa at res.90=(Val, Thr or Ala); Xaa at res.92=(Arg, Lys, Val, Asp or Glu); Xaa at res.93=(Ala, Gly or Glu); and Xaa at res.97=(His or Arg); and Generic Seq. 4:

```
                Generic Sequence 4

Cys Xaa Xaa Xaa Xaa Leu Tyr Val Xaa Phe
        1               5                   10

Xaa Xaa Xaa Gly Trp Xaa Xaa Trp Xaa
                        15

Xaa Ala Pro Xaa Gly Xaa Xaa Ala
        20                  25

Xaa Tyr Cys Xaa Gly Xaa Cys Xaa
                    30                  35

Xaa Pro Xaa Xaa Xaa Xaa Xaa
                        40

Asn Xaa Xaa Asn His Ala Xaa Xaa
                    45              50

Xaa Xaa Leu Xaa Xaa Xaa Xaa Xaa
                        55

Xaa Xaa Xaa Xaa Xaa Xaa Xaa Cys
            60                      65

Cys Xaa Pro Xaa Xaa Xaa Xaa Xaa
                        70

Xaa Xaa Xaa Leu Xaa Xaa Xaa
            75                  80

Xaa Xaa Xaa Xaa Val Xaa Leu Xaa
                        85

Xaa Xaa Xaa Xaa Met Xaa Val Xaa
            90                      95

Xaa Cys Gly Cys Xaa
                    100
``` wherein each Xaa is independently selected from a group of one or more specified amino acids as defined by the following: "Res." means "residue" and Xaa at res.2=(Lys or Arg); Xaa at res.3=(Lys or Arg); Xaa at res.4=(His or Arg); Xaa at res.5=(Glu, Ser, His, Gly, Arg or Pro); Xaa at res.9=(Ser, Arg, Asp or Glu); Xaa at res.11=(Arg, Gln, Ser or Lys); Xaa at res.12=(Asp or Glu); Xaa at res.13=(Leu or Val); Xaa at res.16 (Gln, Leu, Asp, His or Asn); Xaa at res.17=(Asp, Arg, or Asn); Xaa at res.19=(Ile or Val); Xaa at res.20=(Ile or Val); Xaa at res.23=(Glu, Gln, Leu, Lys, Pro or Arg); Xaa at res.25=(Tyr or Phe); Xaa at res.26=(Ala, Ser, Asp, Met, His, Leu, or Gln); Xaa at res.28=(Tyr, Asn or Phe); Xaa at res.31=(Glu, His, Tyr, Asp or Gln); Xaa at res.33=Glu, Lys, Asp or Gln); Xaa at res.35=(Ala, Ser or Pro); Xaa at res.36=(Phe, Leu or Tyr); Xaa at res.38=(Leu or Val); Xaa at res.39=(Asn, Asp, Ala or Thr); Xaa at res.40=(Ser, Asp, Glu, Leu or Ala); Xaa at res.41=(Tyr, Cys, His, Ser or Ile); Xaa at res.42=(Met, Phe, Gly or Leu); Xaa at res.44=(Ala, Ser or Gly); Xaa at res.45=(Thr, Leu or Ser); Xaa at res.49=(Ile or Val); Xaa at res.50=(Val or Leu); Xaa at res.51=(Gln or Arg); Xaa at res.52=(Thr, Ala or Ser); Xaa at res.54=(Val or Met); Xaa at res.55=(His or Asn); Xaa at res.56=(Phe, Leu, Asn, Ser, Ala or Val); Xaa at res.57=(Ile, Met, Asn, Ala or Val); Xaa at res.58=(Asn, Lys, Ala or Glu); Xaa at res.59=(Pro or Ser); Xaa at res.60=(Glu, Asp, or Gly); Xaa at res.61=(Thr, Ala, Val, Lys, Asp, Tyr, Ser or Ala); Xaa at res.62=(Val, Ala or Ile); Xaa at res.63=(Pro or Asp); Xaa at res.64=(Lys or Leu); Xaa at res.65=(Pro or Ala); Xaa at res.68=(Ala or Val); Xaa at res.70=(Thr or Ala); Xaa at res.71=(Gln, Lys, Arg or Glu); Xaa at res.72=(Leu, Met or Val); Xaa at res.73=(Asn, Ser or Asp); Xaa at res.74=(Ala, Pro or Ser); Xaa at res.75=(Ile, Thr or Val); Xaa at res.76=(Ser or Ala); Xaa at res.77=(Val or Met); Xaa at res.79=(Tyr or Phe); Xaa at res.80=(Phe, Tyr or Leu); Xaa at res.81=(Asp or Asn); Xaa at res.82=(Asp, Glu, Asn or Ser); Xaa at res.83=(Ser, Gln, Asn or Tyr); Xaa at res.84=(Ser, Asn, Asp or Glu); Xaa at res.85=(Asn, Thr or Lys); Xaa at res.87=(Ile or Val); Xaa at res.89=(Lys or Arg); Xaa at res.90=(Lys, Asn, Gln or His); Xaa at res.91=(Tyr, Ala or His); Xaa at res.92=(Arg, Gln or Glu); Xaa at res.93=(Asn, Glu or Asp); Xaa at res.95=(Val, Thr or Ala); Xaa at res.97=(Arg, Lys, Val, Asp or Glu); Xaa at res.98=(Ala, Gly or Glu); and Xaa at res.102=(His or Arg).

Particularly useful sequences include the C-terminal residues of Vg1, Vgr-1, DPP, OP-1, OP-2, CBMP-2A, CBMP-2B and GDF-1 (see Table II, infra, and Seq. ID Nos. 5–12) which include at least the conserved six or seven cysteine skeleton. In addition, biosynthetic constructs designed from the generic sequences, such as COP-1, 3-5, 7, 16 (see Table III, infra) also are useful. Others include CBMP3 and the inhibins/activin proteins. Accordingly, other useful sequences are those sharing at least 70% amino acid sequence homology, and preferably 80% homology with any of the sequences above. These are anticipated to include allelic and species variants and mutants, and biosynthetic muteins, as well as novel members of this morphogenic family of proteins.

The invention thus provides proteins comprising any of the polypeptide chains described above, whether isolated from naturally-occurring sources, or produced by recombinant DNA techniques, and includes allelic and species variants of these proteins, naturally-occurring or biosynthetic mutants thereof, as well as various truncated and fusion constructs. Deletion or addition mutants also are envisioned to be active (see infra), including those which may alter the conserved C-terminal cysteine skeleton, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The morphogenic proteins can be expressed from intact or truncated cDNA or from synthetic DNAs in procaryotic or eucaryotic host cells, and purified, cleaved, refolded, and dimerized to form morphogenically active compositions. Currently preferred host cells include *E. coli* or mammalian cells, such as CHO, COS or BSC cells.

Thus, in view of this disclosure, skilled genetic engineers can isolate genes from cDNA or genomic libraries of various different species-which encode appropriate amino acid sequences, or construct DNAs from oligonucleotides, and then can express them in various types of host cells, including both procaryotes and eucaryotes, to produce large quantities of active proteins capable of inducing tissue-specific cell differentiation and tissue morphogenesis in mammals including humans.

The invention thus further comprises these methods of inducing tissue-specific morphogenesis using the morphogenic proteins of this invention.

BRIEF DESCRIPTION OF THE DRAWINGS

The foregoing and other objects and features of this invention, as well as the invention itself, may be more fully understood from the following description, when read together with the accompanying drawings, in which.

DETAILED DESCRIPTION

Figure 1:
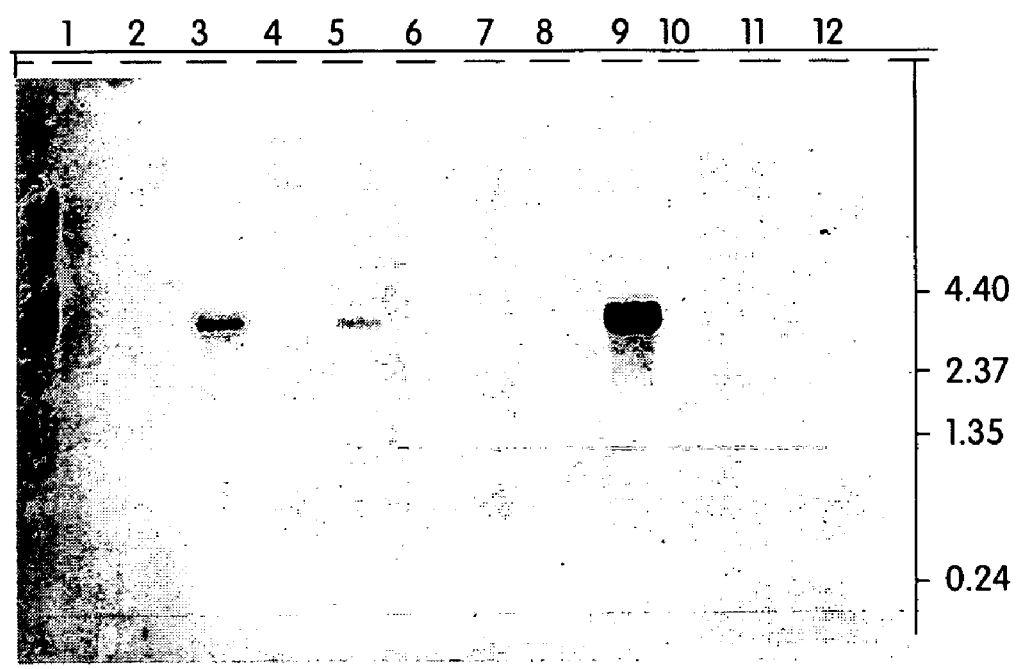
FIG. 1 is a photomicrograph of a Northern Blot identifying Vgr-1 specific transcripts in various adult murine tissues.

Purification protocols first were developed which enabled isolation of the osteogenic (bone inductive) protein present in crude protein extracts from mammalian bone. (See PCT US 89/01453, and U.S. Pat. No. 4,968,590.) The development of the procedure, coupled with the availability of fresh calf bone, enabled isolation of substantially pure bovine osteogenic protein (BOP). BOP was characterized significantly; its ability to induce bone cartilage and ultimately endochondral bone growth in cat, rabbit, and rat were demonstrated and studied; it was shown to be able to induce the full developmental cascade of bone formation previously ascribed to unknown protein or proteins in heterogeneous bone extracts. This dose dependent and highly specific activity was present whether or not the protein was glycosylated (see U.S. Pat. No. 4,968,958, filed Apr. 8, 1988 and Sampath et al., (1990) *J. Biol. Chem.* 265: pp. 13198–13205). Sequence data obtained from the bovine materials suggested probe designs which were used to isolate genes encoding osteogenic proteins from different species. Human and murine OP counterparts have now been identified and characterized (see, for example, U.S. Ser. No. 422,699, filed Oct. 17, 1989 and disclosing DNA and amino acid sequence for human OP-1 ("hOP-1"); U.S. Ser. No. 600,024 filed Oct. 18, 1990, disclosing the murine OP-1 DNA and encoded amino acid sequence ("mOP-1") and U.S. Ser. No. 599,543, filed Oct. 18, 1990), disclosing the human and murine DNA and amino acid sequences for OP-2 ("hOP-2" and mOP-2".)

Sequence data from the bovine materials also suggested substantial homology with a number of proteins known in the art which were not known to play a role in bone formation. Bone formation assays performed with these proteins showed that, when these proteins were implanted in a mammal in association with a suitable matrix, cartilage and endochondral bone formation was induced. (see, for example, U.S. Pat. No. 5,011,691.) One of these proteins is DPP, a Drosophila protein known to play a role in dorsal-ventral specification and required for the correct morphogenesis of the imaginal discs. Two other proteins are related sequences identified in *Xenopus* and mouse (Vg1 and Vgr-1, respectively), thought to play a role in the control of growth and differentiation during embryogenesis. While DPP and Vgr-1 (or Vgr-1-like) transcripts have been identified in a variety of tissues (embryonic, neonatal and adult, Lyons et al., (1989) *PNAS* 86:4554–4558, and see infra), Vg1 transcripts, which are maternally inherited and spacially restricted to the vegetal endoderm, decline dramatically after gastrulation.

From these homologies a generic consensus sequence was derived which encompasses the minimally required active sequence for inducing bone morphogenesis in a mammal when implanted in association with a matrix. The generic sequence has at least a conserved six cysteine skeleton (Generic Sequence 1, Seq. ID No. 1) or, optionally, a 7-cysteine skeleton (Generic Sequence 2, Seq. ID No. 2), where each Xaa indicates any one of the 20 naturally-occurring L-isomer, α-amino acids or a derivative thereof. Longer generic sequences which also are useful further comprise the following sequence at their N-termini:

```
Cys Xaa Xaa Xaa Xaa
 1               5
```

Biosynthetic constructs designed from this generic consensus sequence also have been shown to induce endochondral bone formation (e.g., COP-1, COP-3, COP-4, COP-5, COP-7 and COP-16, see, for example, U.S. Pat. No. 5,011, 691. Table II, set forth below, compares the amino acid sequences of an osteogenically active region of native mature proteins that have been identified as morphogens, including human OP-1 (hOP-1, Seq. ID Nos. 7 and 14), mouse OP-1 (mOP-1, Seq. ID No. 15), human and mouse OP-2 (Seq. ID Nos. 8, 16 and 17), CBMP2a (Seq. ID Nos. 9 and 8), CBMP2b (Seq. ID Nos. 10 and 29), DPP (from *Drosophila*, Seq. ID No. 11), Vg1, (from *Xenopus*, Seq. ID No. 12), and Vgr (from mouse, Seq. ID No. 13). In the table, three dots indicates that the amino acid in that position is the same as the amino acid in hOP-1. Three dashes indicates that no amino acid is present in that position, and are included for purposes of illustrating homologies. For example, amino acid residue 60 of CBMP-2A and CBMP-2B is "missing". Of course, both these amino acid sequences in this region comprise Asn-Ser (residues 58, 59), with CBMP-2A then comprising Lys and Ile, whereas CBMP-2B comprises Ser and Ile.

TABLE II

| | 1 | | | | 5 | | | |
|---|---|---|---|---|---|---|---|---|
| hOP-1 | Cys | Lys | Lys | His | Glu | Leu | Tyr | Val |
| mOP-1 | ... | ... | ... | ... | ... | ... | ... | ... |
| hOP-2 | ... | Arg | Arg | ... | ... | ... | ... | ... |
| mOP-2 | ... | Arg | Arg | ... | ... | ... | ... | ... |
| DPP | ... | Arg | Arg | ... | Ser | ... | ... | ... |
| Vg1 | ... | ... | Arg | ... | His | ... | ... | ... |
| Vgr-1 | ... | ... | ... | ... | Gly | ... | ... | ... |
| CBMP-2A | ... | ... | Arg | ... | Pro | ... | ... | ... |
| CBMP-2B | ... | Arg | Arg | ... | Ser | ... | ... | ... |
| GDF-1 | ... | Arg | Ala | Arg | Arg | ... | ... | ... |

| | | | | 10 | | | | 15 | |
|---|---|---|---|---|---|---|---|---|---|
| hOP-1 | Ser | Phe | Arg | Asp | Leu | Gly | Trp | Gln | Asp |
| mOP-1 | ... | ... | ... | ... | ... | ... | ... | ... | ... |
| hOP-2 | ... | ... | Gln | ... | ... | ... | ... | Leu | ... |
| mOP-2 | Arg | ... | ... | ... | ... | ... | ... | Leu | ... |
| DPP | Asp | ... | Ser | ... | Val | ... | ... | Asp | ... |
| Vg1 | Glu | ... | Lys | ... | Val | ... | ... | ... | Asn |
| Vgr-1 | ... | ... | Gln | ... | Val | ... | ... | ... | ... |
| CBMP-2A | Asp | ... | Ser | ... | Val | ... | ... | Asn | ... |
| CBMP-2B | Asp | ... | Ser | ... | Val | ... | ... | Asn | ... |
| GDF-1 | ... | ... | ... | Glu | Val | ... | ... | His | Arg |

| | | | | | 20 | | | 25 | |
|---|---|---|---|---|---|---|---|---|---|
| hOP-1 | Trp | Ile | Ile | Ala | Pro | Glu | Gly | Tyr | Ala |
| mOP-1 | ... | ... | ... | ... | ... | ... | ... | ... | ... |
| hOP-2 | ... | Val | ... | ... | ... | ... | Gln | ... | Ser |
| mOP-2 | ... | Val | ... | ... | ... | ... | Gln | ... | Ser |
| DPP | ... | Val | ... | ... | ... | ... | Leu | ... | Asp |
| Vg1 | ... | Val | ... | ... | ... | ... | Gln | ... | Met |
| Vgr-1 | ... | ... | ... | ... | ... | ... | Lys | ... | ... |
| CBMP-2A | ... | ... | Val | ... | ... | ... | Pro | ... | His |
| CBMP-2B | ... | ... | Val | ... | ... | ... | Pro | ... | Gln |
| GDF-1 | ... | Val | ... | ... | ... | Arg | ... | Phe | Leu |

| | | | | | | 30 | | 35 | |
|---|---|---|---|---|---|---|---|---|---|
| hOP-1 | Ala | Tyr | Tyr | Cys | Glu | Gly | Glu | Cys | Ala |
| mOP-1 | ... | ... | ... | ... | ... | ... | ... | ... | ... |
| [AhOP-2 | ... | ... | ... | ... | ... | ... | ... | ... | Ser |
| mOP-2 | ... | ... | ... | ... | ... | ... | ... | ... | ... |
| DPP | ... | ... | ... | ... | His | ... | Lys | ... | Pro |
| Vg1 | ... | Asn | ... | ... | Tyr | ... | ... | ... | Pro |
| Vgr-1 | ... | Asn | ... | ... | Asp | ... | ... | ... | Ser |
| CBMP-2A | ... | Phe | ... | ... | His | ... | Glu | ... | Pro |
| CBMP-2B | ... | Phe | ... | ... | His | ... | Asp | ... | Pro |
| GDF-1 | ... | Asn | ... | ... | Gln | ... | Gln | ... | ... |

| | | | | | | | | 40 | |
|---|---|---|---|---|---|---|---|---|---|
| hOP-1 | Phe | Pro | Leu | Asn | Ser | Tyr | Met | Asn | Ala |
| mOP-1 | ... | ... | ... | ... | ... | ... | ... | ... | ... |
| hOP-2 | ... | ... | ... | Asp | ... | Cys | ... | ... | ... |
| mOP-2 | ... | ... | ... | Asp | ... | Cys | ... | ... | ... |
| DPP | ... | ... | ... | Ala | Asp | His | Phe | ... | Ser |
| Vg1 | Tyr | ... | ... | Thr | Glu | Ile | Leu | ... | Gly |
| Vgr-1 | ... | ... | ... | ... | Ala | His | ... | ... | ... |
| CBMP-2A | ... | ... | ... | Ala | Asp | His | Leu | ... | Ser |
| CBMP-2B | ... | ... | ... | Ala | Asp | His | Leu | ... | Ser |
| GDF-1 | Leu | ... | Val | Ala | Leu | Ser | Gly | Ser** | ... |

| | | | | | 45 | | | 50 | |
|---|---|---|---|---|---|---|---|---|---|
| hOP-1 | Thr | Asn | His | Ala | Ile | Val | Gln | Thr | Leu |
| mOP-1 | ... | ... | ... | ... | ... | ... | ... | ... | ... |
| hOP-2 | ... | ... | ... | ... | ... | Leu | ... | Ser | ... |
| mOP-2 | ... | ... | ... | ... | ... | Leu | ... | Ser | ... |
| DPP | ... | ... | ... | ... | ... | Val | ... | ... | ... |
| Vg1 | Ser | ... | ... | ... | ... | ... | ... | ... | ... |
| Vgr-1 | ... | ... | ... | ... | ... | ... | ... | ... | ... |
| CBMP-2A | ... | ... | ... | ... | ... | ... | ... | ... | ... |
| CBMP-2B | ... | ... | ... | ... | ... | ... | ... | ... | ... |
| GDF-1 | Leu | ... | ... | ... | Val | Leu | Arg | Ala | ... |

| | | | | | | | | | |
|---|---|---|---|---|---|---|---|---|---|
| hOP-1 | Val | His | Phe | Ile | Asn | Pro | Glu | Thr | Val |
| mOP-1 | ... | ... | ... | ... | ... | ... | Asp | ... | ... |
| hOP-2 | ... | His | Leu | Met | Lys | ... | Asn | Ala | ... |

TABLE II-continued

| | | | | | | | | |
|---|---|---|---|---|---|---|---|---|
| mOP-2 | ... | His | Leu | Met | Lys | ... | Asp Val | ... |
| DPP | ... | Asn | Asn | Asn | ... | ... | Gly Lys | ... |
| Vg1 | ... | ... | Ser | ... | Glu | ... | ... Asp | Ile |
| Vgr-1 | ... | ... | Val | Met | ... | ... | ... Tyr | ... |
| CBMP-2A | ... | Asn | Ser | Val | ... | Ser | --- Lys | Ile |
| CBMP-2B | ... | Asn | Ser | Val | ... | Ser | --- Ser | Ile |
| GDF-1 | Met | ... | Ala | Ala | Ala | ... | Gly Ala | Ala |
| | | | 55 | | | 60 | | |
| hOP-1 | Pro | Lys | Pro | Cys | Cys | Ala Pro | Thr | Gln |
| mOP-1 | ... | ... | ... | ... | ... | ... | ... | ... |
| hOP-2 | ... | ... | Ala | ... | ... | ... | ... | Lys |
| mOP-2 | ... | ... | Ala | ... | ... | ... | ... | Lys |
| DPP | ... | ... | Ala | ... | ... | Val | ... | ... |
| Vg1 | ... | Leu | ... | ... | ... | Val | ... | Lys |
| Vgr-1 | ... | ... | ... | ... | ... | ... | ... | Lys |
| CBMP-2A | ... | ... | Ala | ... | ... | Val | ... | Glu |
| CBMP-2B | ... | ... | Ala | ... | ... | Val | ... | Glu |
| GDF-1 | Asp | Leu | ... | ... | ... | Val | ... Ala | Arg |
| | | | 65 | | | | 70 | |
| hOP-1 | Leu | Asn | Ala | Ile | Ser | Val Leu Tyr | Phe |
| mOP-1 | ... | ... | ... | ... | ... | ... | ... |
| hOP-2 | .. | Ser | ... | Thr | ... | ... | Tyr |
| mOP-2 | ... | Ser | ... | Thr | ... | ... | Tyr |
| Vg1 | Met | Ser | Pro | ... | ... | Met ... Phe | Tyr |
| Vgr-1 | Val | ... | ... | ... | ... | ... | ... |
| DPP | ... | Asp | Ser | Val | Ala | Met ... | Leu |
| CBMP-2A | ... | Ser | ... | ... | ... | Met ... | Leu |
| CBMP-2B | ... | Ser | ... | ... | ... | Met ... | Leu |
| GDF-1 | ... | Ser | Pro | ... | ... | ... Phe | ... |
| | | | 75 | | | 80 | |
| hOP-1 | Asp | Asp | Ser | Ser | Asn | Val Ile Leu | Lys |
| mOP-1 | ... | ... | ... | ... | ... | ... | ... |
| hOP-2 | ... | Glu | ... | Asn | ... | ... | Arg |
| mOP-2 | ... | Ser | ... | Asn | ... | ... | Arg |
| DPP | Asn | ... | Gln | ... | Thr | ... Val ... | ... |
| Vg1 | ... | ... | Asn | Asp | ... | ... Val ... | Arg |
| Vgr-1 | ... | ... | Asn | ... | ... | ... | ... |
| CBMP-2A | ... | Glu | Asn | Glu | Lys | ... Val ... | ... |
| CBMP-2B | ... | Glu | Tyr | Asp | Lys | ... Val ... | ... |
| GDF-1 | ... | Asn | ... | Asp | ... | ... Val ... | Arg |
| | | | | 85 | | | |
| hOP-1 | Lys | Tyr | Arg | Asn | Met | Val Val Arg |
| mOP-1 | ... | ... | ... | ... | ... | ... |
| hOP-2 | ... | Ala | ... | ... | ... | ... Lys |
| mOP-2 | ... | His | ... | ... | ... | ... Lys |
| DPP | Asn | ... | Gln | Glu | ... | Thr ... Val |
| Vg1 | His | ... | Glu | ... | ... | Ala ... Asp |
| Vgr-1 | ... | ... | ... | ... | ... | ... |
| CBMP-2A | Asn | ... | Gln | Asp | ... | ... Glu |
| CBMP-2B | Asn | ... | Gln | Glu | ... | ... Glu |
| GDF-1 | Gln | ... | Glu | Asp | ... | ... Asp |
| | | 90 | | | | 95 |
| hOP-1 | Ala | Cys | Gly | Cys | His |
| mOP-1 | ... | ... | ... | ... | ... |
| hOP-2 | ... | ... | ... | ... | ... |
| mOP-2 | ... | ... | ... | ... | ... |
| DPP | Gly | ... | ... | ... | Arg |
| Vg1 | Glu | ... | ... | ... | Arg |
| Vgr-1 | ... | ... | ... | ... | ... |
| CBMP-2A | Gly | ... | ... | ... | Arg |
| CBMP-2B | Gly | ... | ... | ... | Arg |
| GDF-1 | Glu | ... | ... | ... | Arg |
| | | | 100 | | |

**Between residues 43 and 44 of GDF-1 lies the amino acid sequence Gly-Gly-Pro-Pro.

Table III, set forth below, compares the amino acid sequence data for six related biosynthetic constructs designated COPs 1, 3, 4, 5, 7, and 16. As with Table II, the dots mean that in that position there is an identical amino acid to that of COP-1, and dashes mean that the COP-1 amino acid is missing at that position.

TABLE III

| | | | | | | | | | |
|---|---|---|---|---|---|---|---|---|---|
| COP-1 | Leu | Tyr | Val | Asp | Phe | Gln | Arg | Asp | Val |
| COP-3 | ... | ... | ... | ... | ... | ... | ... | ... | ... |
| COP-4 | ... | ... | ... | ... | ... | ... | Ser | --- | ... | ... |
| COP-5 | ... | ... | ... | ... | ... | ... | Ser | --- | ... | ... |
| COP-7 | ... | ... | ... | ... | ... | ... | Ser | --- | ... | ... |
| COP-16 | ... | ... | ... | ... | ... | ... | Ser | --- | ... | ... |
| | 1 | | | | 5 | | | | |
| COP-1 | Gly | Trp | Asp | Asp | Trp | Ile | Ile | Ala |
| COP-3 | ... | ... | ... | ... | ... | ... | Val | ... |
| COP-4 | ... | ... | ... | ... | ... | ... | Val | ... |
| COP-5 | ... | ... | ... | ... | ... | ... | Val | ... |
| COP-7 | ... | ... | Asn | ... | ... | ... | Val | ... |
| COP-16 | ... | ... | Asn | ... | ... | ... | Val | ... |
| | 10 | | | | | 15 | | |

TABLE III-continued

```
COP-1   Pro  Val  Asp  Phe  Asp  Ala  Tyr  Tyr
COP-3   ...  Pro  Gly  Tyr  Gln  ...  Phe  ...
COP-4   ...  Pro  Gly  Tyr  Gln  ...  Phe  ...
COP-5   ...  Pro  Gly  Tyr  Gln  ...  Phe  ...
COP-7   ...  Pro  Gly  Tyr  His  ...  Phe  ...
COP-16  ...  Pro  Gly  Tyr  Gln  ...  Phe  ...
              20                  25

COP-1   Cys  Ser  Gly  Ala  Cys  Gln  Phe  Pro
COP-3   ...  ...  ...  ...  ...  ...  ...  ...
COP-4   ...  ...  ...  ...  ...  ...  ...  ...
COP-5   ...  His  ...  Glu  ...  Pro  ...  ...
COP-7   ...  His  ...  Glu  ...  Pro  ...  ...
COP-16  ...  His  ...  Glu  ...  Pro  ...  ...
                        30

COP-1   Ser  Ala  Asp  His  Phe  Asn  Ser  Thr
COP-3   ...  ...  ...  ...  ...  ...  ...  ...
COP-4   ...  ...  ...  ...  ...  ...  ...  ...
COP-5   Leu  ...  ...  ...  ...  ...  ...  ...
COP-1   Leu  ...  ...  ...  Leu  ...  ...  ...
COP-16  Leu  ...  ...  ...  ...  ...  ...  ...
              35                  40

COP-1   Asn  His  Ala  Val  Val  Gln  Thr  Leu  Val
COP-3   ...  ...  ...  ...  ...  ...  ...  ...  ...
COP-4   ...  ...  ...  ...  ...  ...  ...  ...  ...
COP-5   ...  ...  ...  ...  ...  ...  ...  ...  ...
COP-7   ...  ...  ...  ...  ...  ...  ...  ...  ...
COP-16  ...  ...  ...  ...  ...  ...  ...  ...  ...
                        45                  50

COP-1   Asn  Asn  Met  Asn  Pro  Gly  Lys  Val
COP-3   ...  ...  ...  ...  ...  ...  ...  ...
COP-4   ...  ...  ...  ...  ...  ...  ...  ...
COP-5   ...  Ser  Val  ...  Ser  Lys  Ile  ...
COP-1   ...  Ser  Val  ...  Ser  Lys  Ile  ...
COP-16  ...  Ser  Val  ...  Ser  Lys  Ile  ...
                             55

COP-1   Pro  Lys  Pro  Cys  Cys  Val  Pro  Thr
COP-3   ...  ...  ...  ...  ...  ...  ...  ...
COP-4   ...  ...  ...  ...  ...  ...  ...  ...
COP-5   ...  ...  Ala  ...  ...  ...  ...  ...
COP-1   ...  ...  Ala  ...  ...  ...  ...  ...
COP-16  ...  ...  Ala  ...  ...  ...  ...  ...
              60                  65

COP-1   Glu  Leu  Ser  Ala  Ile  Ser  Met  Leu
COP-3   ...  ...  ...  ...  ...  ...  ...  ...
COP-4   ...  ...  ...  ...  ...  ...  ...  ...
COP-5   ...  ...  ...  ...  ...  ...  ...  ...
COP-7   ...  ...  ...  ...  ...  ...  ...  ...
COP-16  ...  ...  ...  ...  ...  ...  ...  ...
                             70

COP-1   Tyr  Leu  Asp  Glue Asn  Ser  Thr  Val
COP-3   ...  ...  ...  ...  ...  Glu  Lys  ...
COP-4   ...  ...  ...  ...  ...  Glu  Lys  ...
COP-5   ...  ...  ...  ...  ...  Glu  Lys  ...
COP-7   ...  ...  ...  ...  ...  Glu  Lys  ...
COP-16  ...  ...  ...  ...  ...  Glu  Lys  ...
              75                  80

COP-1   Val  Leu  Lys  Asn  Tyr  Gln  Glu  Met
COP-3   ...  ...  ...  ...  ...  ...  ...  ...
COP-4   ...  ...  ...  ...  ...  ...  ...  ...
COP-5   ...  ...  ...  ...  ...  ...  ...  ...
COP-7   ...  ...  ...  ...  ...  ...  ...  ...
COP-16  ...  ...  ...  ...  ...  ...  ...  ...
                        85                  90

COP-1   Thr  Val  Val  Gly  Cys  Gly  Cys  Arg
COP-3   Val  ...  Glu  ...  ...  ...  ...  ...
COP-4   Val  ...  Glu  ...  ...  ...  ...  ...
COP-5   Val  ...  Glu  ...  ...  ...  ...  ...
COP-7   Val  ...  Glu  ...  ...  ...  ...  ...
COP-16  Val  ...  Glu  ...  ...  ...  ...  ...
                             95
```

As is apparent from the foregoing amino acid sequence comparisons, significant amino acid changes can be made within the generic sequences while retaining the morphogenic activity. For example, the GDF-1 protein shares approximately 70% amino acid sequence homology with the collection of sequences defined by Table II.

It now has been discovered that the family of proteins described by these sequences also is capable of initiating and maintaining the tissue-specific developmental cascade in tissues other than bone and bone cartilage. When combined with naive progenitor cells as disclosed herein, these proteins, termed morphogens, are capable of inducing the proliferation and differentiation of the progenitor cells. In the presence of appropriate tissue-specific signals to direct the differentiation of these cells, and a morphogenically permissive environment, these morphogens are capable of reproducing the cascade of cellular and molecular events that occur during embryogenesis development to yield adult, functioning tissue.

A key to these developments was the creation of a mammalian tissue model system, namely a model system for endochondral bone formation, and investigation of the cascade of events important for bone tissue morphogenesis. Work on this system has enabled discovery not only of bone inductive morphogens, but also of tissue inductive morphogens and their activities. The methods used to develop the bone model system, now well known in the art, along with the proteins of this invention, can be used to create model systems for other tissues, such as liver (see infra).

Using the model system for endochondral bone formation, it also has been discovered that the local environment in which the morphogenic material is placed is important for tissue morphogenesis. As used herein, "local environment" is understood to include the tissue structural matrix and the environment surrounding the tissue. For example, in addition to needing an appropriate anchoring substratum for their proliferation, the morphogen-stimulated cells need signals to direct the tissue-specificity of their differentiation. These signals vary for the different tissues and may include cell surface markers. In addition, vascularization of new tissue requires a local environment which supports vascularization. Using the bone model system as an example, it is known that, under standard assay conditions, implanting osteoinductive morphogens into loose mesenchyme in the absence of a tissue-specifying matrix generally does not result in endochondral bone formation unless very high concentrations of the protein are implanted. By contrast, implanting relatively low concentrations of the morphogen in association with a suitably modified bone-derived matrix is results in the formation of fully functional endochondral bone (see, for example, Sampath et al. (1981) *PNAS* 78:7599–7603 and U.S. Pat. No. 4,975,526). In addition, a synthetic matrix comprised of a structural polymer such as tissue-specific collagen and tissue-specific cell attachment factors such as tissue-specific glycosylaminoglycans, will allow endochondral bone formation (see, for example, U.S. Ser. No. 529,582, filed May 30, 1990, incorporated herein by reference). Finally, if the morphogen and a suitable bone or bone cartilage-specific matrix (e.g., comprising Type I cartilage) are implanted together in loose mesenchyme, bone cartilage and endochondral bone formation will result, including the formation of bone marrow and a vascular system. However, if the same composition is provided to a nonvascular environment, such as to cultured cells in vitro or at an cartilage-specific locus, tissue development does not continue beyond cartilage formation (see infra). Similarly, a morphogenic composition containing a cartilage-specific matrix composed of Type 2 collagen is expected to induce formation of non-bone cartilage tissue in vivo (e.g., hyaline). However, if the composition is provided to a vascular-supporting environment, such as loose mesenchyme, the composition is capable of inducing the differentiation of proliferating progenitor cells into chondrocytes and osteoblasts, resulting in bone formation.

It also has been discovered that tissue morphogenesis requires a morphogenically permissive environment. Clearly, in fully-functioning healthy tissue that is not composed of a permanently renewing cell population, there must exist signals to prevent continued tissue growth. Thus, it is postulated that there exists a control mechanism, such as a feedback control mechanism, which regulates the control of cell growth and differentiation. In fact, it is known that both TGF-β, and MIS are capable of inhibiting cell growth when present at appropriate concentrations. In addition, using the bone model system it can be shown that osteogenic devices comprising a bone-derived carrier (matrix) that has been demineralized and guanidine-extracted to substantially remove the noncollagenous proteins does allow endochondral bone formation when implanted in association with an osteoinductive morphogen. If, however, the bone-derived carrier is not demineralized but rather is washed only in low salt, for example, induction of endochondral bone formation is inhibited, suggesting the presence of one or more inhibiting factors within the carrier.

Another key to these developments was determination of the broad distribution of these morphogens in developing and adult tissue. For example, DPP is expressed in both embryonic and developing *Drosophila* tissue. Vg1 has been identified in *Xenopus* embryonic tissue. Vgr-1 transcripts have been identified in a variety of murine tissues, including embryonic and developing brain, lung, liver, kidney and calvaria (dermal bone) tissue. Recently, Vgr-1 transcripts also have been identified in adult murine lung, kidney, heart, and brain tissue, with especially high abundance in the lung (see infra).

OP-1 and the CBMP2 proteins, both first identified as bone morphogens, have been identified in mouse and human placenta, hippocampus, calvaria and osteosarcoma tissue as determined by identification of OP-1 and CMBP2-specific sequences in cDNA libraries constructed from these tissues (see U.S. Ser. No. 422,699, incorporated herein by reference). Additionally, the OP-1 protein is present in a variety of embryonic and developing tissues including kidney, liver, heart, adrenal tissue and brain as determined by Western blot analysis and immunolocalization (see infra and Ser. No. 07/752,861). OP-1-specific transcripts also have been identified in both embryonic and developing tissues, most abundantly in developing kidney, bladder and brain (see infra). OP-1 also has been identified as a mesoderm inducing factor present during embryogenesis (see infra). Moreover, OP-1 has been shown to be associated with in satellite muscle cells and associated with pluripotential stem cells in bone marrow following damage to adult murine endochondral bone, indicating its morphogenic role in tissue repair and regeneration. In addition, a novel protein GDF-1 (see Table II) has been identified in neural tissue (Lee, (1991) *PNAS* 88 4250–4254).

Exemplification

Identification and Isolation of Morphogens

Among the proteins useful in this invention are proteins originally identified as bone inductive proteins, such as the OP-1, OP-2 and the CBMP proteins, as well as amino acid sequence related proteins such as DPP (from *Drosophila*), Vg1 (from *Xenopus*) and Vgr-1 (from mouse, see Table II and Sequence Listing). The members of this family, which include some members of the TGF-β super family of structurally related proteins, share substantial amino acid sequence homology in their C-terminal regions. The OP-2 proteins have an extra cysteine residue in this region (position 41), in addition to the conserved cysteine skeleton in common with the other proteins in this family. The proteins are inactive when reduced, but are active as oxidized homodimers and as various oxidized heterodimers.

Accordingly, the morphogens of this invention can be described by either of the following two species of generic amino acid sequences: Generic Sequence 1 or Generic Sequence 2, (Seq. ID Nos. 1 and 2), where each Xaa indicates one of the 20 naturally-occurring L-isomer, α-amino acids or a derivative thereof. Particularly useful sequences that fall within this family of proteins include the 102 C-terminal residues of Vg1, Vgr-1, DPP, OP-1, OP-2, CBMP-2A, and CBMP-2B, as well as their intact mature amino acid sequences. 7–19). In addition, biosynthetic constructs designed from the generic sequences, such as COP-1, COP-3-5, COP-7, and COP-16 also are useful.

Generic sequences showing preferred amino acids compiled from sequences identified to date as useful as morphogens (e.g., Tables II and III) are described as: Generic Sequence 3 (Seq. ID No. 3) and Generic Sequence 4 (Seq. ID No. 4). Note that these generic sequences have a 7 or 8-cysteine skeleton where inter- or intramolecular disulfide bonds can form, and contain certain critical amino acids which influence the tertiary structure of the proteins. It is also possible that the differing N-termini of the naturally occurring proteins provide a tissue-specific or other, important modulating activity of these proteins.

Given the foregoing amino acid and DNA sequence information, the level of skill in the art, and the disclosure of U.S. Pat. No. 5,011,691 and published PCT specification US 89/01469, published Oct. 19, 1989, the disclosures of which are incorporated herein by reference, various DNAs can be constructed which encode at least the minimally required active domain of a morphogen of this invention, and various analogs thereof (including allelic variants and those containing genetically engineered mutations), as well as fusion proteins, truncated forms of the mature proteins, deletion and insertion mutants, and similar constructs. Moreover, DNA hybridization probes can be constructed from fragments of the genes encoding any of these proteins, or designed de novo from the generic sequence. These probes then can be used to screen different genomic and cDNA libraries to identify additional morphogenic proteins from different tissues.

The DNAs can be produced by those skilled in the art using well known DNA manipulation techniques involving genomic and cDNA isolation, construction of synthetic DNA from synthesized oligonucleotides, and cassette mutagenesis techniques. 15–100 mer oligonucleotides may be synthesized on a Biosearch DNA Model 8600 Synthesizer, and purified by polyacrylamide gel electrophoresis (PAGE) in Tris-Borate-EDTA buffer. The DNA then may be electroeluted from the gel. Overlapping oligomers may be phosphorylated by T4 polynucleotide kinase and ligated into larger blocks which also may be purified by PAGE.

The DNA from appropriately identified clones then can be isolated, subcloned (preferably into an expression vector), and sequenced. Plasmids containing sequences of interest then can be transfected into an appropriate host cell for expression of the morphogen and further characterization. The host may be a procaryotic or eucaryotic cell since the former's inability to glycosylate protein will not destroy the protein's morphogenic activity. Useful host cells include *E. coli*, *Saccharomyces*, the insect/baculovirus cell system, myeloma cells, and various other mammalian cells. The vectors additionally may encode various sequences to promote correct expression of the recombinant protein, including transcription promoter and termination sequences, enhancer sequences, preferred ribosome binding site sequences, preferred mRNA leader sequences, preferred signal sequences for protein secretion, and the like.

The DNA sequence encoding the gene of interest also may be manipulated to remove potentially inhibiting sequences or to minimize unwanted secondary and tertiary structure formation. The recombinant morphogen also may be expressed as a fusion protein. After being translated, the protein may be purified from the cells themselves or recovered from the culture medium. All biologically active protein forms comprise dimeric species joined by disulfide bonds or otherwise associated, produced by refolding and oxidizing one or more of the various recombinant polypeptide chains within an appropriate eucaryotic cell or in vitro after expression of individual subunits. A detailed description of morphogens expressed from recombinant DNA in *E. coli* is disclosed in U.S. Ser. No. 422,699 filed Oct. 17, 1989, the disclosure of which is incorporated herein by reference. A detailed description of morphogens expressed from recombinant DNA in numerous different mammalian cells is disclosed in U.S. Ser. No. 569,920 filed Aug. 20, 1990, the disclosure of which is hereby incorporated by reference.

Alternatively, morphogenic polypeptide chains can be synthesized chemically using conventional peptide synthesis techniques well known to those having ordinary skill in the art. For example, the proteins may be synthesized intact or in parts on a Biosearch solid phase peptide synthesizer, using standard operating procedures. Completed chains then are deprotected and purified by HPLC (high pressure liquid chromatography). If the protein is synthesized in parts, the parts may be peptide bonded using standard methodologies to form the intact protein. In general, the manner in which the morphogens are made can be conventional and does not form a part of this invention.

Morphogen Distribution

The generic function of the morphogens of this invention throughout the life of the organism can be evidenced by their expression in a variety of disparate mammalian tissues. Determination of the tissue distribution of morphogens also may be used to identify different morphogens expressed in a given tissue, as well as to identify new, related morphogens. The proteins (or their mRNA transcripts) are readily identified in different tissues using standard methodologies and minor modifications thereof in tissues where expression may be low. For example, protein distribution may be determined using standard Western blot analysis or immunofluorescent techniques, and antibodies specific to the morphogen or morphogens of interest. Similarly, the distribution of morphogen transcripts may be determined using standard Northern hybridization protocols and transcript-specific probes.

Any probe capable of hybridizing specifically to a transcript, and distinguishing the transcript of interest from other, related transcripts may be used. Because the morphogens of this invention share such high sequence homology in their active, C-terminal domains, the tissue distribution of a specific morphogen transcript may best be determined using a probe specific for the pro region of the immature protein and/or the N-terminal region of the mature protein. Another useful sequence is the 3' non-coding region flanking and immediately following the stop codon. These portions of the sequence vary substantially among the morphogens of this invention, and accordingly, are specific for each protein. For example, a particularly useful Vgr-1-specific probe sequence is the PvuII-SacI fragment, a 265 bp fragment encoding both a portion of the untranslated pro region and the N-terminus of the mature sequence (see Lyons et al. (1989) *PNAS* 86:4554–4558 for a description of the cDNA sequence). Similarly, particularly useful mOP-1-specific probe sequences are the BstX1-BglI fragment, a 0.68 Kb sequence that covers approximately two-thirds of the mOP-1 pro region; a StuI-StuI fragment, a 0.2 Kb sequence immediately upstream of the 7-cysteine domain; and the EarI-PstI fragment, an 0.3 Kb fragment containing a portion of the 3'untranslated sequence (See Seq. ID No. 15).

Using these morphogen-specific probes, which may be synthetically engineered or obtained from cloned sequences, morphogen transcripts can be identified in mammalian tissue, using standard methodologies well known to those having ordinary skill in the art. Briefly, total RNA is prepared from various adult murine tissues (e.g., liver, kidney, testis, heart, brain, thymus and stomach) by a stand and methodology such as by the method of Chomczyaski et al. ((1987) *Anal. Biochem* 162:156–159) and described below. Poly (A)+ RNA is prepared by using oligo (dT)-cellulose chromatography (e.g., Type 7, from Pharmacia LKB Biotechnology, Inc.). Poly (A)+ RNA (generally 15 µg) from each tissue is fractionated on a 1% agarose/formaldehyde gel and transferred onto a Nytran membrane (Schleicher & Schuell). Following the transfer, the membrane is baked at 80° C. and the RNA is cross-linked under UV light (generally 30 seconds at 1 mW/cm$^2$). Prior to hybridization, the appropriate probe (e.g., the PvuII-SacI Vgr-1 fragment) is denatured by heating. The hybridization is carried out in a lucite cylinder rotating in a roller bottle apparatus at approximately 1 rev/min for approximately 15 hours at 37° C. using a hybridization mix of 40% formamide, 5× Denhardts, 5×SSPE, and 0.1% SDS. Following hybridization, the non-specific counts are washed off the filters in 0.1× SSPE, 0.1% SDS at 50° C. Northern blots performed using Vgr-1 probes specific to the variable N terminus of the mature sequence indicate that the Vgr-1 message is approximately 3.5 Kb.

FIG. 1 is a photomicrograph representing a Northern blot analysis probing a number of adult murine tissues with the Vgr-1 specific probes: liver, kidney, testis, heart, brain, thymus and stomach, represented in lanes 3–10, respectively. Lanes 1 and 12 are size standards and lanes 2 and 11 are blank. Among the tissues tested, Vgr-1 appears to be expressed most abundantly in adult lung, and to a lesser extent in adult kidney, heart and brain. These results confirm and expand on earlier studies identifying Vgr-1 and Vgr-1-like transcripts in several embryonic and adult murine tissue (Lyons et al. (1989) *PNAS* 86:4554–4558), as well as studies identifying OP-1 and CBMP2 in various human cDNA libraries (e.g., placenta, hippocampus, calvaria, and osteosarcoma, see U.S. Ser. No. 422,699, filed Oct. 17, 1989, and Ozkaynak et al., (1990) *EMBO* 9:2085–2093).

Figure 2:
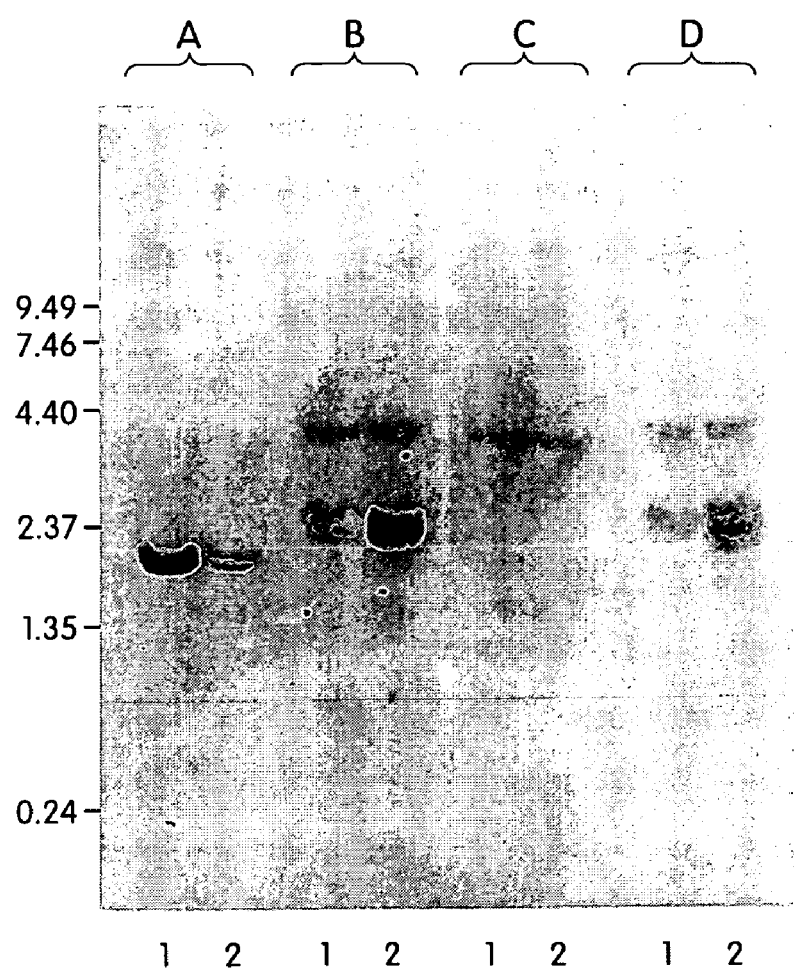
FIG. 2 is a photomicrograph of a Northern Blot identifying mOP-1-specific mRNA expression in various murine tissues prepared from 2 week old mice (panel A) and 5 week old mice (Panel B)
Figure 3:
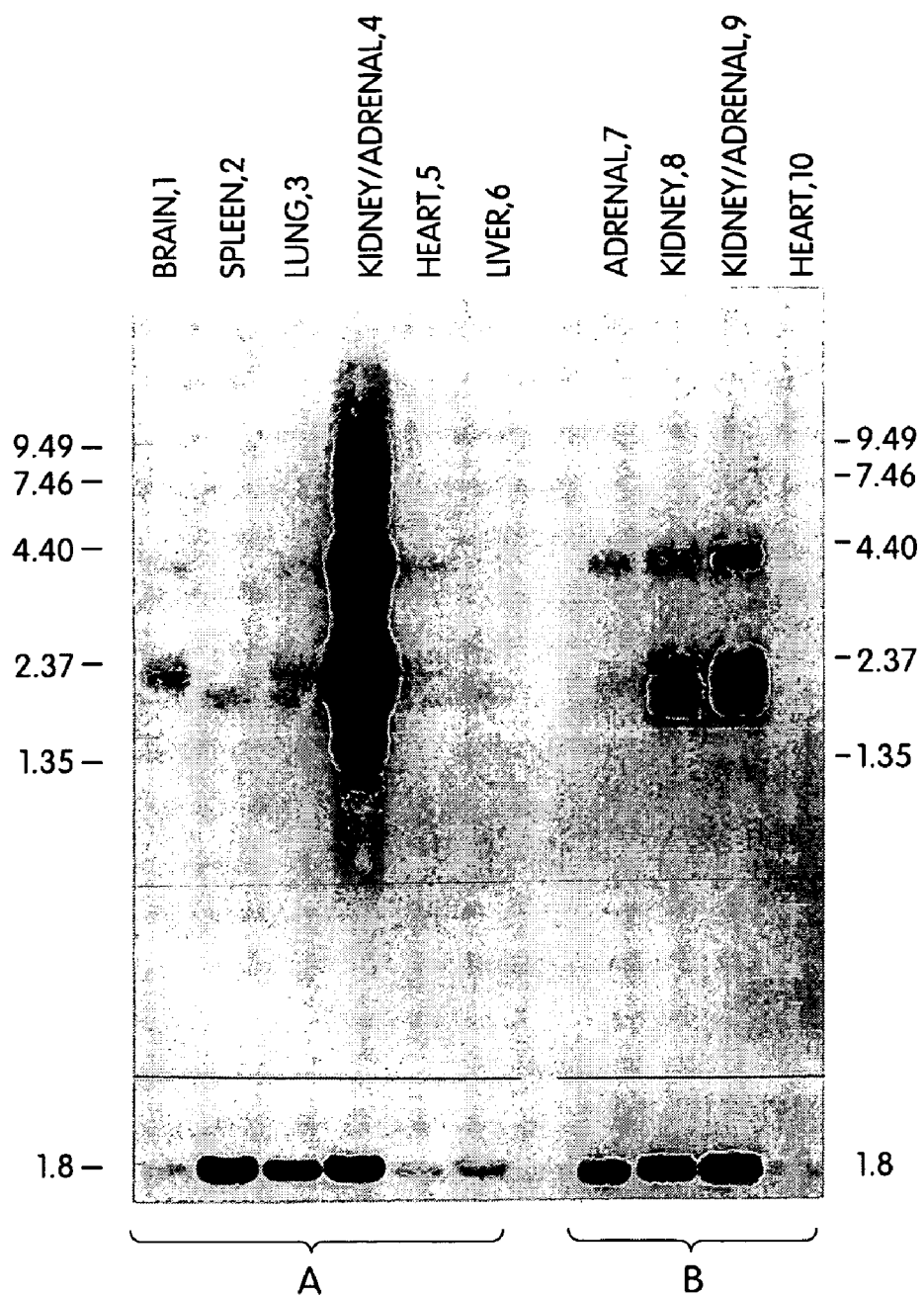
FIG. 3 is a photomicrograph of Northern Blots identifying mRNA expression of EF-Tu (A, control), mOP-1 (B, D), and Vgr-1 (C) in (1) 17-day embryos and (2) 3-day post natal mice.

Using the same general probing methodology, mOP-1 transcripts also have been identified in a variety of murine tissues, including embryo and various developing tissues, as can be seen in FIGS. 2 and 3. Details of the probing methodology are disclosed in Ser. No. 07/752,861, the disclosure of which is incorporated herein. The Northern blots represented in FIG. 2 probed RNA prepared from developing brain, spleen, lung, kidney (and adrenal gland), heart, and liver in 13 day post natal mice (panel A) or 5 week old mice (panel B). The OP-1 specific probe was a probe containing the 3' untranslated sequences described supra (0.34 Kb EarI-Pst I fragment). As a control for RNA recovery, EF-Tu (translational elongation factor) mRNA expression also was measured (EF-Tu expression is assumed to be relatively uniform in most tissues).

The arrowheads indicate the OP-1 specific messages observed in the various tissues. As can be seen in FIG. 2, OP-1 expression levels vary significantly in the spleen, lung, kidney and adrenal tissues, while the EF-Tu mRNA levels are constant. Uniformly lower levels of EF-Tu mRNA levels were found in the heart, brain and liver. As can be seen from the photomicrograph, the highest levels of OP-1 mRNA appear to be in kidney and adrenal tissue, followed by the brain. By contrast, heart and liver did not give a detectable signal. Not shown are additional analyses performed on bladder tissue, which shows significant OP-1 mRNA expression, at levels close to those in kidney/adrenal tissue. The Northern blots also indicate that, like GDF-1, OP-1 mRNA expression may be bicistonic in different tissues. Four transcripts can be seen: 4 Kb, 2.4 Kb, 2.2 Kb, and 1.8 Kb transcripts can be identified in the different tissues, and cross probing with OP-1 specific probes from the proregion and N-terminal sequences of the gene indicate that these transcripts are OP-1 specific.

A side by side comparison of OP-1 and Vgr-1 in FIG. 3 shows that the probes distinguish between the morphogens Vgr-1 and OP-1 transcripts in the different tissues, and also highlights the multiple transcription of OP-1 in different tissues. Specifically, FIG. 3 compares the expression of OP-1 (Panels B and D), Vgr-1 (Panel C) and EF-Tu (Panel A) (control) mRNA in 17 day embryos (lane 1) and 3 day post-natal mice (lane 2). The same filter was used for sequential hybridizations with labeled DNA probes specific for OP-1 (Panels B and D), Vgr-i (Panel C), and EF-Tu (Panel A). Panel A: the EF-Tu specific probe (control) was the 0.4 Kb HindIII-SacI fragment (part of the protein coding region), the SacI site used belonged to the vector; Panel B: the OP-1 specific probe was the 0.68 Kb BstXI-BglI fragment containing pro region sequences; Panel D; the OP-1 specific probe was the 0.34 Kb EarI-PstI fragment containing the 3' untranslated sequence; Panel C: the Vgr-1 specific probe was the 0.26 Kb PvuII-SacI fragment used in the Vgr-1 blots described above.

The 1.8–2.5 Kb OP-1 mRNA appears approximately two times higher in three day post natal mice than in 17 day embryos, perhaps reflecting phases in bone and/or kidney development. In addition, of the four messages found in brain, the 2.2 Kb transcript appears most abundant, whereas in lung and spleen the 1.8 Kb message predominates. Finally, careful separation of the renal and adrenal tissue in five week old mice reveals that the 2.2 Kb transcripts were derived from renal tissue and the 4 Kb mRNA is more prominent in adrenal tissue (see FIG. 2).

Similarly, using the same general probing methodology, BMP3 and CBMP2B transcripts recently have been identified in abundance in lung tissue.

Morphogen distribution in embryonic tissue can be determined using five or six-day old mouse embryos and standard immunofluorescence techniques in concert with morphogen-specific antisera. For example, rabbit anti-OP-1 antisera is readily obtained using any of a number of standard antibody protocols well known to those having ordinary skill in the art. The antibodies then are fluorescently labelled using standard procedures. A five or six-day old mouse embryo then is thin-sectioned and the various developing tissues probed with the labelled antibody, again following standard protocols. Using this technique, OP-1 protein is detected in developing brain and heart.

This method also may be used to identify morphogens in adult tissues undergoing repair. For example, a fracture site can be induced in a rat long bone such as the femur. The fracture then is allowed to heal for 2 or 3 days. The animal then is sacrificed and the fractured site sectioned and probed for the presence of the morphogen e.g., OP-1, with fluorescently labelled rabbit anti-OP-1 antisera using standard immunblocalization methodology. This technique identifies OP-1 in muscle satellite cells, the progenitor cells for the development of muscle, bone cartilage and endochondral bone. In addition, OP-1 is detected with potential pluripotential stem cells in the bone marrow, indicating its morphogenic role in tissue repair and regeneration.

OP-1 protein also has been identified in rat brain using standard immunofluorescence staining technique. Specifically, adult rat brain (2–3 months old) and spinal cord is frozen and sectioned. Anti-OP-1, raised in rabbits and purified on an OP-1 affinity column prepared using standard methodologies, was added to the sections under standard conditions for specific binding. Goat anti-rabbit IgG, labelled with fluorescence, then was used to visualize OP-1 antibody binding to tissue sections.

Figure 4A:
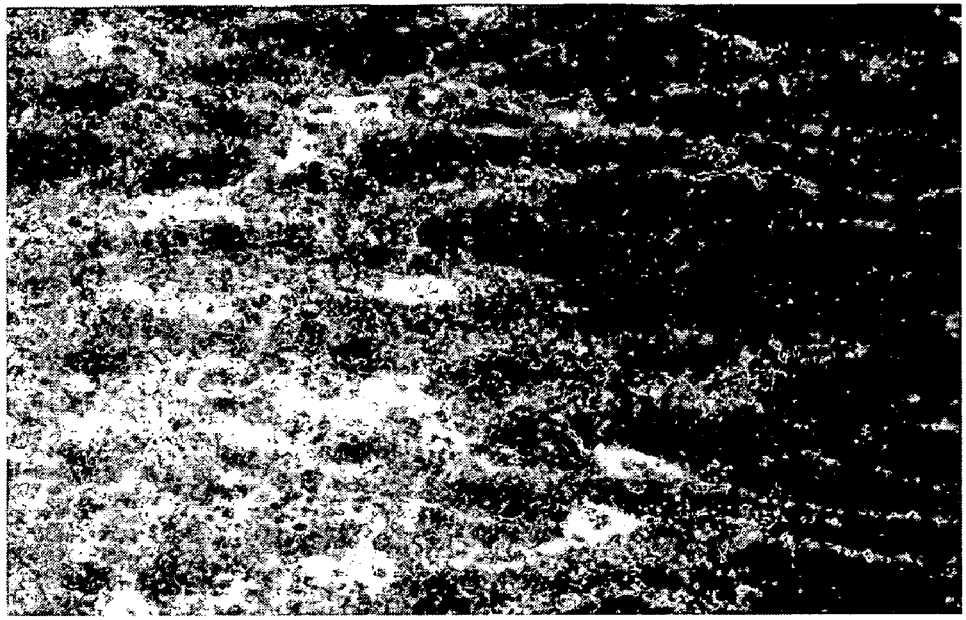
FIGS. 4A and 4B are photomicrographs showing the presence of OP-1 (by immunofluorescence staining) in the cerebral cortex (A) and spinal cord (B)
Figure 4B:
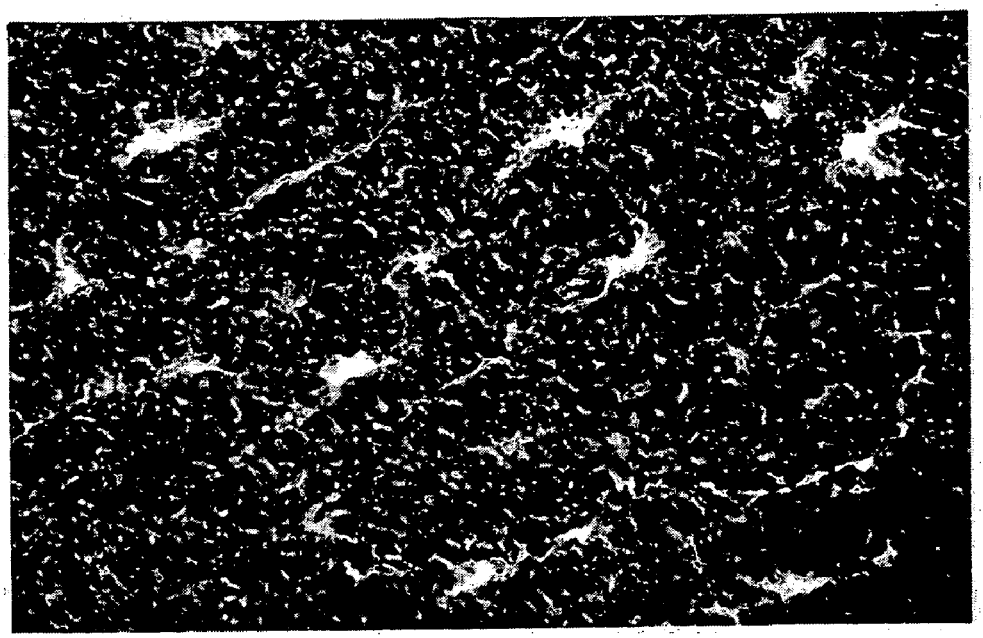

As can be seen in FIGS. 4A and 4B, immunofluorescence staining demonstrates the presence of OP-1 in adult rat CNS. Similar and extensive staining is seen in both the brain (4A) and spinal cord (4B). OP-1 appears to be predominantly localized to the extracellular matrix of the grey matter, present in all areas except the neuronal cell bodies. In white matter, staining appears to be confined to astrocytes. A similar staining pattern also was seen in newborn rat (10 day old) brain sections.

Cell Differentiation

The ability of morphogens of this invention to induce cell differentiation can be determined by culturing early mesenchymal cells in the presence of the morphogen and then studying the histology of the cultured cells by staining with toluidine blue. For example, it is known that rat mesenchymal cells destined to become mandibular bone, when separated from the overlying epithelial cells at stage 11 and cultured in vitro under standard tissue culture conditions, will not continue to differentiate. However, if these same cells are left in contact with the overlying endoderm for an additional day, at which time they become stage 12 cells, they will continue to differentiate on their own in vitro to form chondrocytes. Further differentiation into obsteoblasts and, ultimately, mandibular bone, requires an appropriate local environment, e.g., a vascularized environment.

It has now been discovered that stage 11 mesenchymal cells, cultured in vitro in the presence of a morphogen, e.g., OP-1, continue to differentiate in vitro to form chondrocytes. These stage 11 cells also continue to differentiate in vitro if they are cultured with the cell products harvested from the overlying endodermal cells. Moreover, OP-1 can be identified in the medium conditioned by endodermal cells either by Western blot or immunofluorescence. This experiment may be performed with other morphogens and with different mesenchymal cells to assess the cell differentiation capability of different morphogens, as well as their distribution in different developing tissues.

As another example of morphogen-induced cell differentiation, the effect of OP-1 on the differentiation of neuronal cells has been tested in culture. Specifically, the effect of OP-1 on the NG108-5 neuroblastoma x glioma hybrid clonal cell line has been assessed. The cell line shows a fibroblastic-type morphology in culture. The cell line can be induced to differentiate chemically using 0.5 mM butyrate, 1% DMSO or 500 mM Forskolin, inducing the expression of virtually all important neuronal properties of cultured primary neurons. However, chemical induction of these cells also induces cessation of cell division.

Figure 5A:
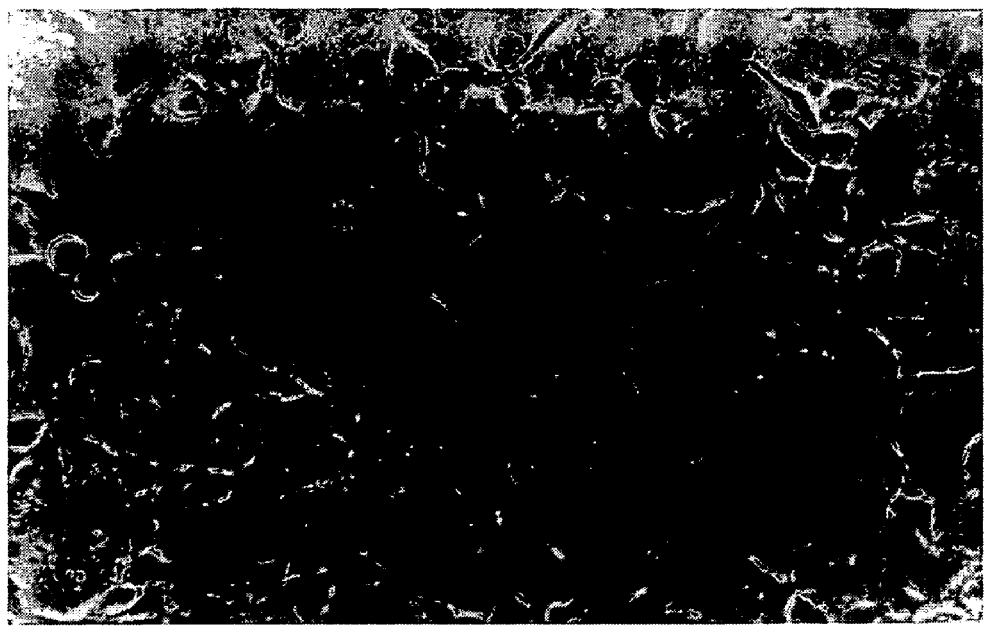
FIGS. 5A and 5B are photomicrographs illustrating the ability of morphogen (OP-1) to induce undifferentiated NG108 calls (5A) to undergo differentiation of neural morphology (5B).
Figure 5B:
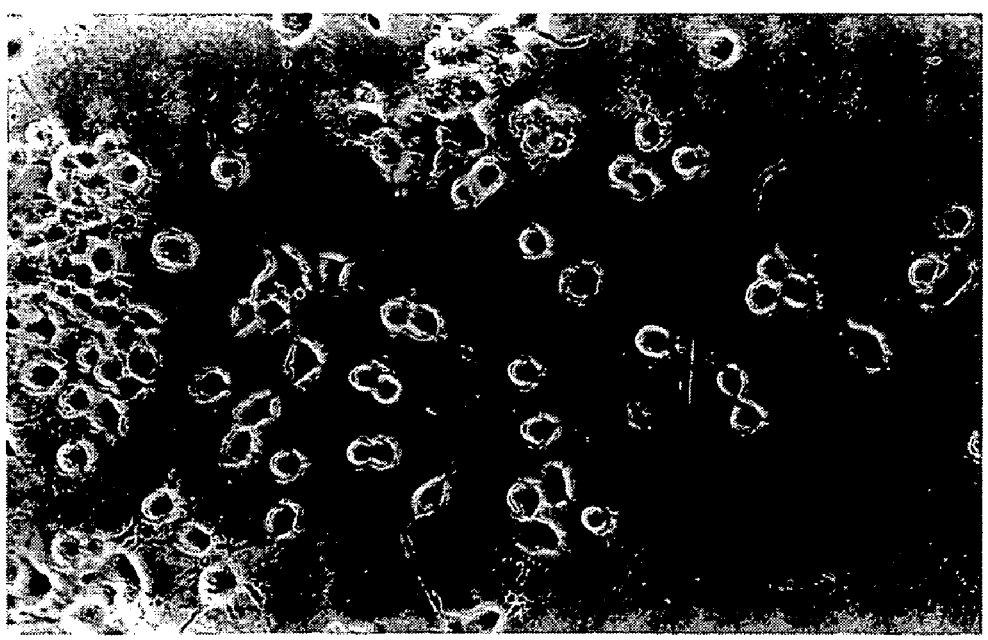

In the present experiment NG108-5 cells were subcultured on poly-L-lysine coated 6 well plates. Each well contained 40–50,000 cells in 2.5 ml of chemically defined medium. On the third day 2.5 µl of OP-1 in 60% ethanol containing 0.025% trifluoroacetic was added to each well. OP-1 concentrations of 0, 1, 10, 40 and 100 ng/ml were tested. The media was changed daily with new aliquots of OP-1. After four days with 40 and 100 ng OP-1/ml concentrations, OP-1 induced differentiation of NG108 cells. FIG. 5 shows the morphological changes that occur. The OP-1 induces clumping and rounding of the cells and the production of neurite outgrowths (processes). Compare FIG. 5A (naive NG108 cells) with FIG. 5B, showing the effects of OPI-treated cells. Thus the OP-1 can induce the cells to differentiate into a neuronal cell morphology. Some of the outgrowths appear to join in a synaptic-type junction. This effect was not seen in cells incubated with TGF-B1 at concentrations of 1 to 100 ng/ml.

The neuroprotective effects of OP-1 were demonstrated by comparison with chemical differentiation agents on the NG108 cells. 50,000 cells were plated on 6 well plates and treated with butyrate, DMSO, Forskolin or OP-1 for four days. Cell counts demonstrated that in the cultures containing the chemical agents the differentiation was accompanied by a cessation of cell division. In contrast, the cells induced to differentiate by OP-1 continued to divide, as determined by $H^3$-thymidine uptake. The data suggest that OP-1 is capable of maintaining the stability of the cells in culture after differentiation.

Figure 6A:
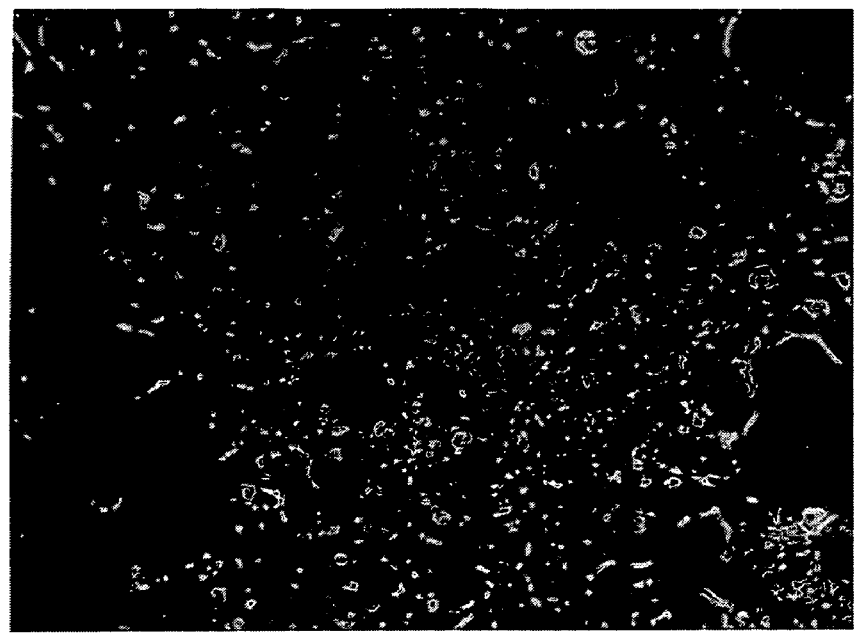
FIGS. 6A–6D are photomicrographs showing the effect of morphogen (OP-1) on human embryo carcinoma cell rediferentiation.
Figure 6B:
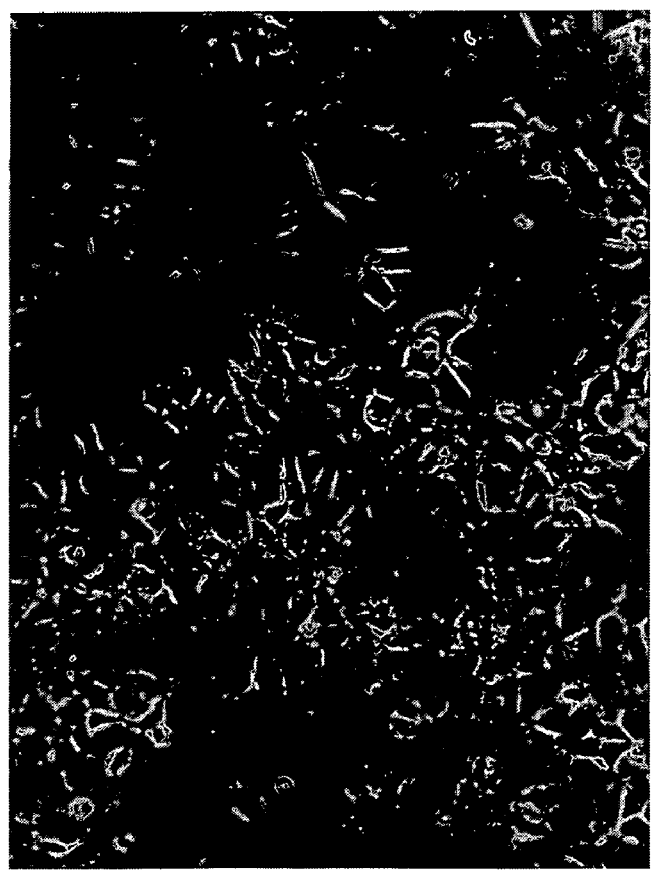
Figure 6C:
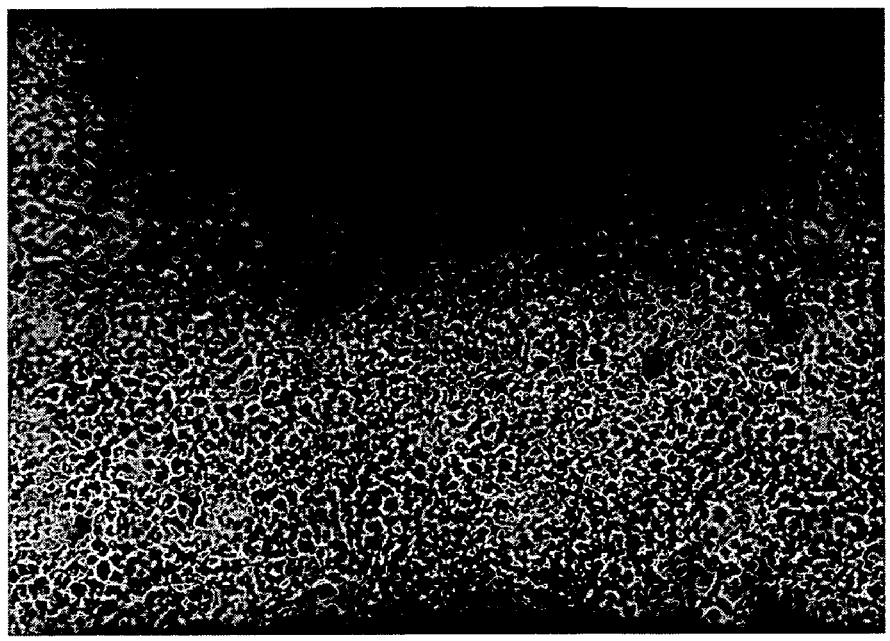
Figure 6D:
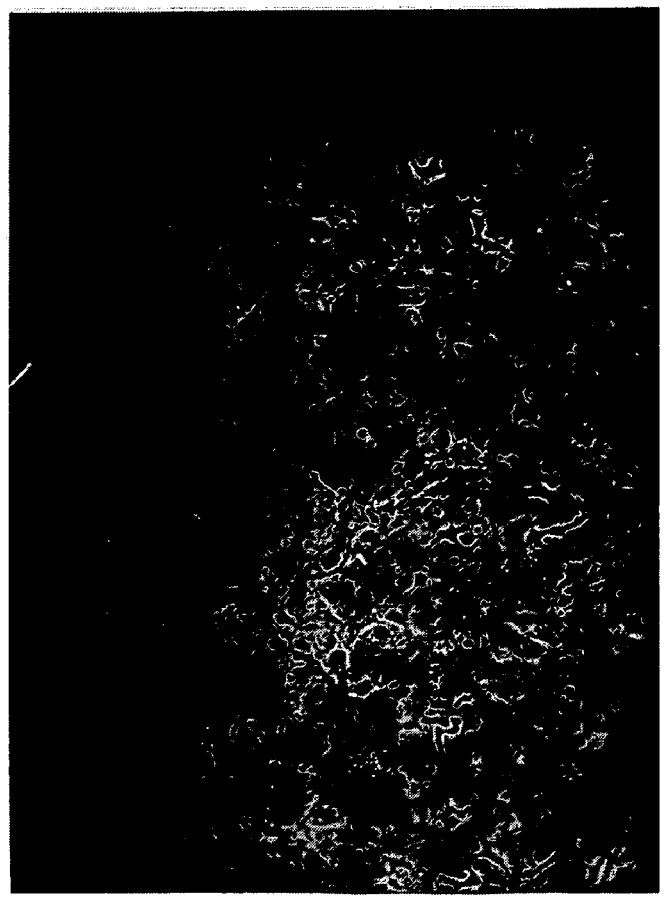

As yet another, related example, the ability of the morphogens of this invention to induce the "redifferentiation" of transformed cells also has been assessed. Specifically, the effect of OP-1 on human EC cells (embryo carcinoma cells, NTERA-Z CL.D1) is disclosed herein. In the absence of an external stimulant these cells can be maintained as undifferentiated stem cells, and can be induced to grow in serum free media (SFM). In the absence of morphogen treatment the cells proliferate rampantly and are anchorage-independent. The effect of morphogen treatment is seen in FIGS. 6A–D. FIGS. 6A and 6B show 4 days of growth in SFM in the presence of OP-1 (25 ng/ml, 6A) or the absence of morphogen (6B). FIGS. 6C and 6D are 5 days growth in the presence of 10 ng/ml OP-1 (6C) or no morphogen (6D). FIGS. 6C and 6D are at 10× and 20× magnification compared to FIGS. 6A and 5B. As can readily be seen, in the presence of OP-1, EC cells grow as flattened cells, becoming anchorage dependent. In addition, growth rate is reduced approximately 10 fold. Finally, the cells are induced to differentiate.

Maintenance of Phenotype

The morphogens of this invention also may be used to maintain a cell's differentiated phenotype. This morphogenic capability is particularly useful for inducing the continued expression of phenotype in senescent or quiescent cells.

The phenotypic maintenance capability of morphogens is readily assessed. A number of differentiated cells become senescent or quiescent after multiple passages under standard tissue culture conditions in vitro. However, if these cells are cultivated in vitro in association with a morphogen of this invention, the cells are induced to maintain expression of their phenotype through multiple passages. For example, the alkaline phosphatase activity of cultured osteoblasts, like cultured osteoscarcoma cells and calvaria cells, is significantly reduced after multiple passages in vitro. However, if the cells are cultivated in the presence of a morphogen (e.g., OP-1), alkaline phosphatase activity is maintained over extended periods of time. Similarly, phenotypic expression of myocytes also is maintained in the presence of the morphogen. This experiment may be performed with other morphogens and different cells to assess the phenotypic maintenance capability of different morphogens on cells of differing origins.

Phenotypic maintenance capability also may be assessed in vivo, using a rat model for osteoporosis, disclosed in Ser. No. 07/752,857, incorporated herein by reference. As disclosed therein, Long Evans rats are ovariectomized to produce an osteoporotic condition resulting from decreased estrogen production. Eight days after ovariectomy, rats are systemically provided with phosphate buffered saline (PBS) or OP-1 (21 µg or 20 µg) for 22 days. The rats then are sacrificed and and serum alkaline phosphatase levels, serum calcium levels, and serum osteocalcin levels determined, using standard methodologies. Three-fold higher levels of osteocalcin levels are found in rats provided with 1 or 20 µg of OP-1. Increased alkaline phosphatase levels also were seen. Histomorphometric analysis on the tibial diaphysical bone shows OP-1 can reduce bone mass lost due to the drop in estrogen levels.

Cell Stimulation

The ability of the morphogens of this invention to stimulate the proliferation of progenitor cells also can be assayed readily in vitro. Useful naive stem cells include pluripotential stem cells, which may be isolated from bone marrow or umbilical cord blood using conventional methodologies, (see, for example, Faradji et al., (1988) *Vox Sanq.* 55 (3):133–138 or Broxmeyer et al., (1989) *PNAS* 86 (10): 3828–3832), as well as naive stem cells obtained from blood. Alternatively, embryonic cells (e.g., from a cultured mesodermal cell line) may be useful.

Another method for obtaining progenitor cells and for determining the ability of morphogens to stimulate cell proliferation is to capture progenitor cells from an in vivo source. For example, a biocompatible matrix material able to allow the influx of migratory progenitor cells may be implanted at an in vivo site long enough to allow the influx of migratory progenitor cells. For example, a bone-derived, guanidine-extracted matrix, formulated as disclosed for example in Sampath et al. ((1983) *PNAS* 80:6591–6595), or U.S. Pat. No. 4,975,526, may be implanted into a rat at a subcutaneous site, essentially following the method of Sampath et al. (ibid). After three days the implant is removed, and the progenitor cells associated with the matrix dispersed and cultured.

Progenitor cells, however obtained, then are incubated in vitro with a suspected morphogen under standard cell culture conditions well known to those having ordinary skill in the art. In the absence of external stimuli, the progenitor cells do not, or minimally proliferate on their own in culture. However, if the cells are cultured in the presence of a morphogen, such as OP-1, they are stimulated to proliferate. Cell growth can be determined visually or spectrophotometrically using standard methods well known in the art.

Proliferation of Progenitor Cell Populations

Progenitor cells may be stimulated to proliferate in vivo or ex vivo. The cells may be stimulated in vivo by injecting or otherwise providing a sterile preparation containing the morphogen into the individual. For example, the hemopoietic pluripotential stem cell population of an individual may be stimulated to proliferate by injecting or otherwise providing an appropriate concentration of the morphogen to the individual's bone marrow.

Progenitor cells may be stimulated ex vivo by contacting progenitor cells of the population to be enhanced with a morphogen under sterile conditions at a concentration and for a time sufficient to stimulate proliferation of the cells. In general, a period of from about 10 minutes to about 24 hours should be sufficient. The stimulated cells then are provided to the individual as, for example, by injecting the cells to an appropriate in vivo locus. Suitable biocompatible progenitor cells may be obtained by any of the methods known in the art or described herein.

Regeneration of Damaged or Diseased Tissue

The morphogens of this invention may be used to repair diseased or damaged mammalian tissue. The tissue to be repaired is preferably assessed, and excess necrotic or interfering scar tissue removed as needed, by surgical, chemical, ablating or other methods known in the medical arts.

The morphogen then may be provided directly to the tissue locus as part of a sterile, biocompatible composition, either by surgical implantation or injection. Alternatively, a sterile, biocompatible composition containing morphogen-stimulated progenitor cells may be provided to the tissue locus. The existing tissue at the locus, whether diseased or damaged, provides the appropriate matrix to allow the proliferation and tissue-specific differentiation of progenitor cells. In addition, a damaged or diseased tissue locus, particularly one that has been further assaulted by surgical means, provides a morphogenically permissive environment. For some tissues, it is envisioned that systemic provision of the morphogen will be sufficient.

In some circumstances, particularly where tissue damage is extensive, the tissue may not be capable of providing a sufficient matrix for cell influx and proliferation. In these instances, it may be necessary to provide the morphogen or morphogen-stimulated progenitor cells to the tissue locus in association with a suitable, biocompatible formulated matrix, prepared by any of the means described below. The matrix preferably is tissue-specific, in vivo biodegradable, and comprises particles having dimensions within the range of 70–850 µm, most preferably 150–420 µm.

The morphogens of this invention also may be used to prevent or substantially inhibit scar tissue formation following an injury. If a morphogen is provided to a newly injured tissue locus, it can induce tissue morphogenesis at the locus, preventing the aggregation of migrating fibroblasts into non-differentiated connective tissue. The morphogen preferably is provided as a sterile pharmaceutical preparation injected into the tissue locus within five hours of the injury. Several non-limiting examples follow, illustrating the morphogens regenerate capabilities in different issues. The proteins of this invention previously have been shown to be capable of inducing cartilage and endochondral bone formation (See, for example U.S. Pat. No. 5,011,691).

As an example, protein-induced morphogenesis of substantially injured liver tissue following a partial hepatectomy is disclosed. Variations on this general protocol may be used to test morphogen activity in other different tissues. The general method involves excising an essentially nonregenerating portion of a tissue and providing the morphogen, preferably as a soluble pharmaceutical preparation to the excised tissue locus, closing the wound and examining the site at a future date. Like bone, liver has a potential to regenerate upon injury during post-fetal life.

Morphogen, (e.g., purified recombinant human OP-1, mature form, was solubilized (1 mg/ml) in 50% ethanol (or compatible solvent) containing 0.1% trifluoroacetic acid (or compatible acid). The injectable OP-1 solution was prepared by diluting one volume of OP-1/solvent-acid stock solution with 9 volumes of 0.2% rat serum albumin in sterile PBS (phosphate-buffered saline).

Growing rats or aged rats were anesthetized by using ketamine. Two of the liver lobes (left and right) were cut out (approximately ⅓ of the lobe) and the OP-1 was injected locally at multiple sites along the cut ends. The amount of OP-1 injected was 100 μg in 100 of PBS/RSA injection buffer. Placebo samples are injection buffer without OP-1. Five rats in each group were used. The wound was closed and the rats were allowed to eat normal food and drink tap water.

Figure 7:
FIG. 7 is a photomicrograph showing the effects of phosphate buffered saline (PBS, animal 1) or morphogen (OP-1, animal 2) on partially hepatectomized rats.

After 12 days, the rats were sacrificed and liver regeneration was observed visually. The photomigraph in FIG. 7 illustrates dramatically the regenerative effects of OP-1 on liver regeneration. The OP-1-injected group showed complete liver tissue regeneration and showed no sign of any cut in the liver (animal 2). By contrast, the control group into which only PBS only was injected, although some amount of regeneration was seen, lack of complete liver regeneration was evident (animal 1). The incision remains in this sample.

As another example, the ability of the morphogens of this invention to induce dentinogenesis also was assessed. To date, the unpredictable response of dental pulp tissue to injury is a basic clinical problem in dentistry. Cynomolgus monkeys were chosen as primate models as monkeys are presumed to be more indicative of human dental biology than models based on lower non-primate mammals.

Using standard dental surgical procedures, small areas (e.g., 2 mm) of dental pulps were surgically exposed by removing the enamel and dentin immediately above the pulp (by drilling) of sample teeth, performing a partial amputation of the coronal pulp tissue, inducing hemostasis, application of the pulp treatment, and sealing and filling the cavity by standard procedures.

Figure 8A:
FIGS. 8A–8C are photomicrographs showing the effect of no treatment (8A), carrier matrix treatment (8B) and morphogen treatment (OP-1,8C) on dentin regeneration.
Figure 8B:
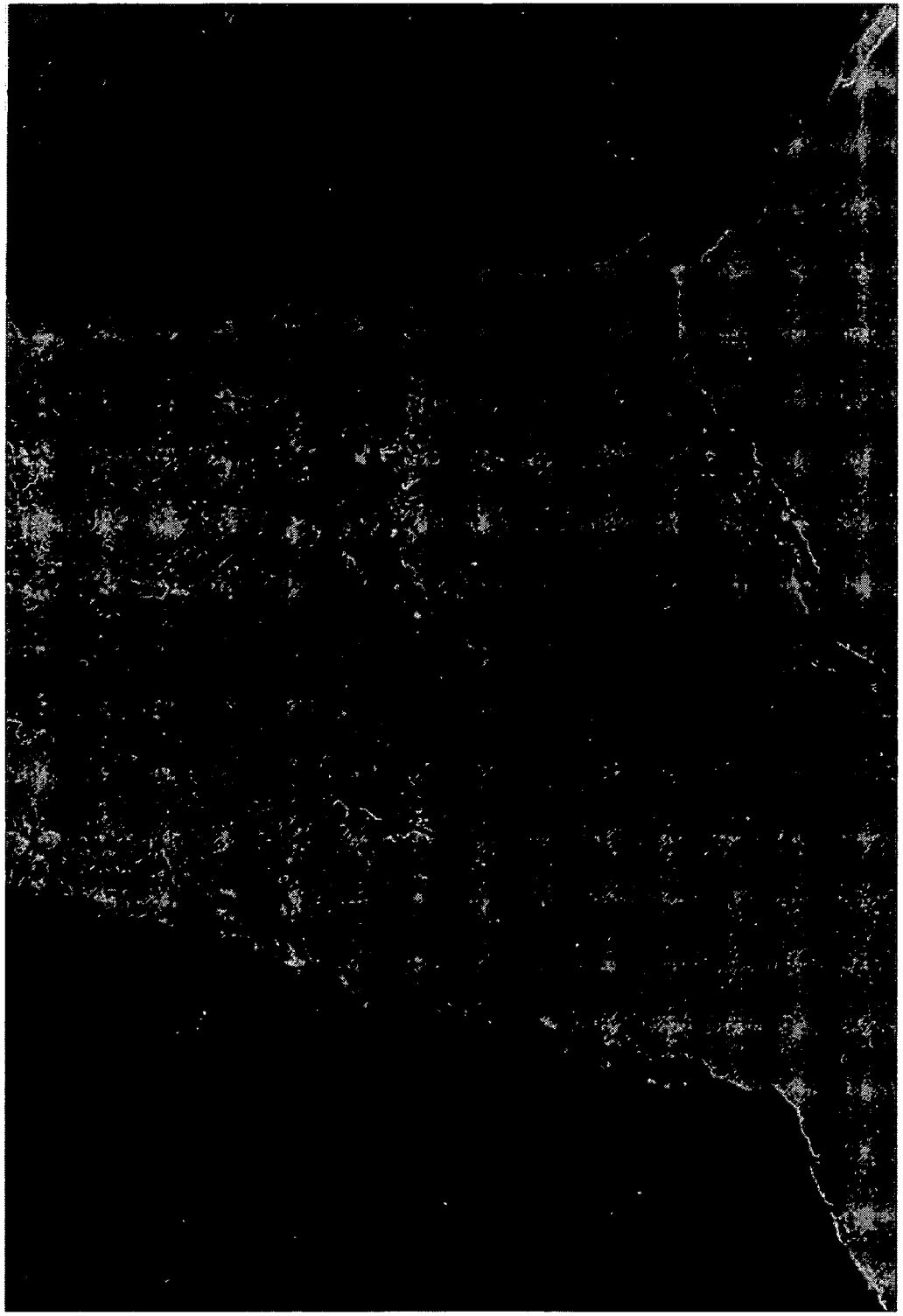
Figure 8C:
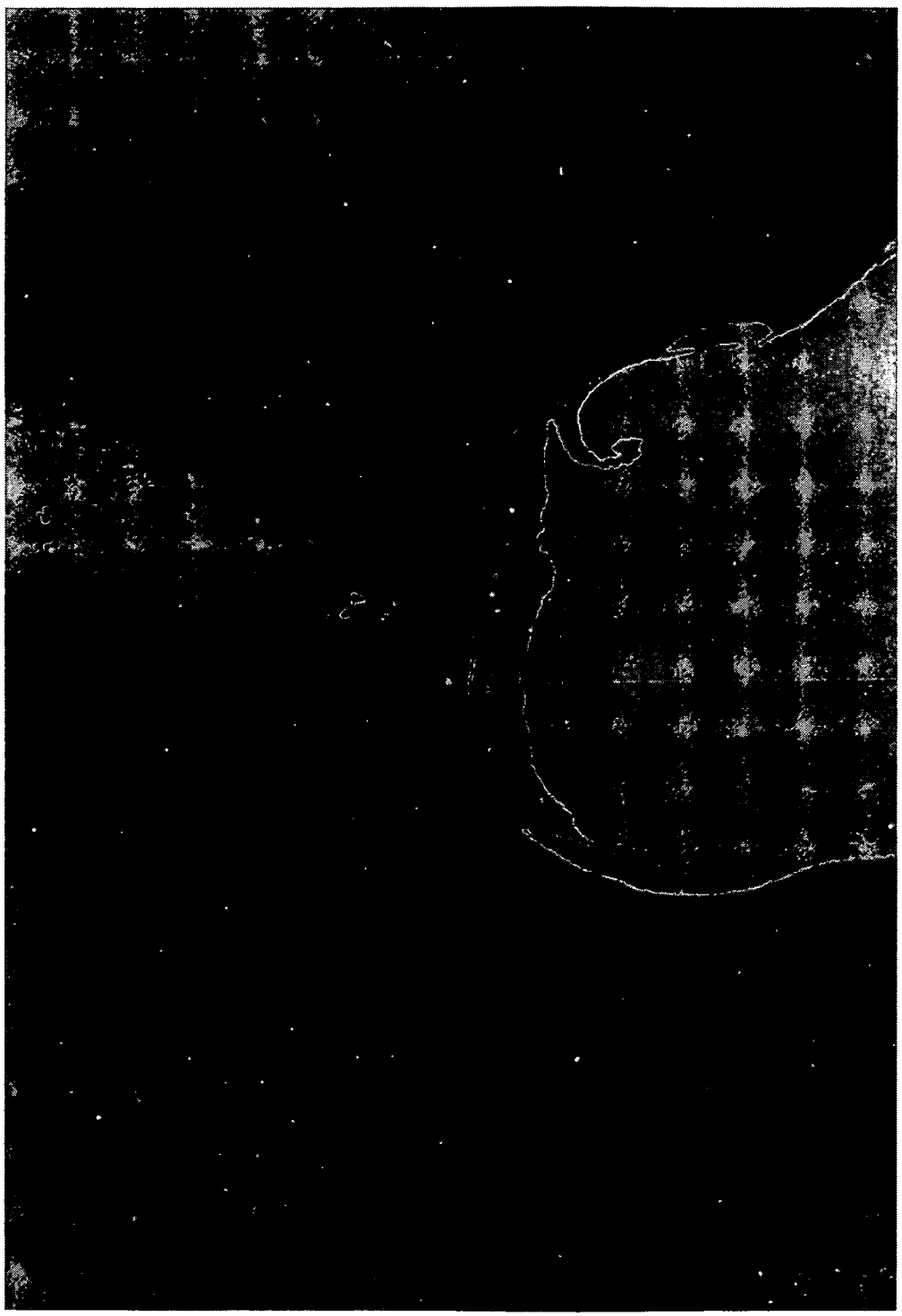

Pulp treatments used were: OP-1 dispersed in a carrier matrix; carrier matrix alone and no treatment. Twelve teeth per animal (four for each treatment) were prepared, and two animals were used. At four weeks, teeth were extracted and processed histologically for analysis of dentin formation, and/or ground to analyze dentin mineralization. FIG. 8 illustrates dramatically the effect of morphogen on osteodentin reparation. FIG. 8A is a photomicrograph of the control treatment (PBS) and shows little or no reparation. FIG. 8B is a photomicrograph of treatment with carrier alone, showing minimal reparation. By contrast, treatment with morphogen (FIG. 8C) shows significant reparation. The results of FIG. 8 indicate that OP-1-CM (OP-1 plus carrier matrix) reliably induced formation of reparative or osteodentin bridges on surgically exposed healthy dental pulps. By contrast, pulps treated with carrier matrix alone, or not treated failed to form reparative dentin.

As another example, the morphogen-induced regenerative effects on central nervous system (CNS) repair may be assessed using a rat brain stab model. Briefly, male Long Evans rats are anesthesized and the head area prepared for surgery. The calvariae is exposed using standard surgical procedures and a hole drilled toward the center of each lobe using a 0.035 K wire, just piercing the calvariae. 25 μl solutions containing either morphogen (OP-1, 25 μg) or PBS then is provided to each of the holes by Hamilton syringe. Solutions are delivered to a depth approximately 3 mm below the surface, into the underlying cortex, corpus callosum and hippocampus. The skin then is sutured and the animal allowed to recover.

Three days post surgery, rats are sacrificed by decapitation and their brains processed for sectioning. Scar tissue formation is evaluated by immunofluoresence staining for glial fibrillary acidic protein, a marker protein for glial scarring, to qualitatively determine the degree of scar formation. Sections also are probed with anti-OP-1 antibodies to determine the presence of OP-1.

Morphogen Activity Modulation

Antibodies to morphogens of this invention have been identified in healthy human sera. In addition, implanting devices comprising morphogen (e.g., OP-1) have been discovered to induce an increase in anti-morphogen antibodies (e.g., anti, anti-OP antibodies). It is anticipated that these antibodies comprise part of the body's regulation of morphogen activity in vivo. The presence of the antibodies, and fluctuations in their levels, which are readily monitored, can provide a useful method for monitoring tissue stasis and tissue viability (e.g., identification of a pathological state). For example, standard radioimmunoassays or ELISA may be used to detect and quantify antibodies in sera. These antibodies may be raised against isolated morphogens using standard methodologies.

Matrix Preparation

The morphogens of this invention may be implanted surgically, dispersed in a biocompatible, preferably in vivo biodegradable matrix appropriately modified to provide a structure in which the morphogen may be dispersed and which allows the influx, differentiation and proliferation of migrating progenitor cells. The matrix also should provide signals capable of directing the tissue specificity of the differentiating cells, as well as a morphogenically permissive environment, being essentially free of growth inhibiting signals.

In the absence of these features the matrix does not appear to be suitable as part of a morphogenic composition. Recent studies on osteogenic devices (morphogens dispersed within a formulated matrix) using matrices formulated from polylactic acid and/or polyglycolic acid biopolymers, ceramics (a-tri-calcium-phosphate), or hydroxyapatite show that these materials, by themselves, are unable to provide the appropriate environment for inducing de novo endochondral bone formation in rats by themselves. In addition, matrices formulated from commercially available highly purified, reconstituted collagens or naturally-derived non-bone, species-specific collagen (e.g., from rat tail tendon) also are unsuccessful in inducing bone when implanted in association with an osteogenic protein. These matrices apparently lack specific structurally-related features which aid in directing the tissue specificity of the morphogen-stimulated, differentiating progenitor cells.

The formulated matrix may be shaped as desired in anticipation of surgery or may be shaped by the physician or technician during surgery. Thus, the material may be used in topical, subcutaneous, intraperitoneal, or intramuscular implants to repair tissue or to induce its growth de novo. The matrix preferably is biodegradable in vivo, being slowly absorbed by the body and replaced by new tissue growth, in the shape or very nearly in the shape of the implant.

Details of how to make and how to use the matrices useful in this invention are disclosed below.

Tissue-derived Matrices

Suitable biocompatible, in vivo biodegradable acellular matrices may be prepared from naturally-occurring tissue. The tissue is treated with suitable agents to substantially extract the cellular, nonstructural components of the tissue. The agents also should be capable of extracting any growth inhibiting components associated with the tissue. The resulting material is a porous, acellular matrix, substantially depleted in nonstructurally-associated components.

The matrix also may be further treated with agents that modify the matrix, increasing the number of pores and micropits on its surfaces. Those skilled in the art will know how to determine which agents are best suited to the extraction of nonstructural components for different tissues. For example, soft tissues such as liver and lung may be thin-sectioned and exposed to a nonpolar solvent such as, for example, 100% ethanol, to destroy the cellular structure of the tissue and extract nonstructural components. The material then is dried and pulverized to yield nonadherent porous particles. Structural tissues such as cartilage and dentin where collagen is the primary component may be demineralized and extracted with guanidine, essentially following the method of Sampath et al. (1983) *PNAS* 80:6591–6595. For example, pulverized and demineralized dentin is extracted with five volumes of 4 M guanidine-HCl, 50 mM Tris-HCl, pH 7.0 for 16 hours at 4° C. The suspension then is filtered. The insoluble material that remains is collected and used to fabricate the matrix. The material is mostly collagenous in manner. It is devoid of morphogenic activity. The matrix particles may further be treated with a collagen fibril-modifying agent that extracts potentially unwanted components from the matrix, and alters the surface structure of the matrix material. Useful agents include acids, organic solvents or heated aqueous media. A detailed description of these matrix treatments are disclosed in U.S. Pat. No. 4,975,526 and copending U.S. Ser. No. 483,913, filed Feb. 22, 1990 and incorporated herein by reference.

After contact with the fibril-modifying agent, the treated matrix may be washed to remove any extracted components, following a form of the procedure set forth below:

1. Suspend matrix preparation in TBS (Tris-buffered saline) 1 g/200 ml and stir at 4° C. for 2 hrs; or in 6 M urea, 50 mm Tris-HCl, 500 mM NaCl, pH 7.0 (UTBS) or water and stir at room temperature (RT) for 30 minutes (sufficient time to neutralize the pH);

2. Centrifuge and repeat wash step; and

3. Centrifuge; discard supernatant; water wash residue; and then lyophilize.

Synthetic Tissue-specific Matrices

In addition to the naturally-derived tissue-specific matrices described above, useful tissue-specific matrices may be formulated synthetically if appropriately modified. These porous biocompatible, in vivo biodegradable synthetic matrices are disclosed in copending U.S. Ser. No. 529,852, filed May 30, 1990, the disclosure of which is hereby incorporated by reference. Briefly, the matrix comprises a porous crosslinked structural polymer of biocompatible, biodegradable collagen and appropriate, tissue-specific glycosaminoglycans as tissue-specific cell attachment factors. Collagen derived from a number of sources may be suitable for use in these synthetic matrices, including insoluble collagen, acid-soluble collagen, collagen soluble in neutral or basic aqueous solutions, as well as those collagens which are commercially available.

Glycosaminoglycans (GAGs) or mucopolysaccharides are hexosamine-containing polysaccharides of animal origin that have a tissue specific distribution, and therefore may be used to help determine the tissue specificity of the morphogen-stimulated differentiating cells. Reaction with the GAGs also provides collagen with another valuable property, i.e., inability to provoke an immune reaction (foreign body reaction) from an animal host.

Chemically, GAGs are made up of residues of hexoamines glycosidically bound and alternating in a more-or-less regular manner with either hexouronic acid or hexose moieties (see, e.g., Dodgson et al. in *Carbohydrate Metabolism and its Disorders* (Dickens et al., eds.) Vol. 1, Academic Press (1968)). Useful GAGs include hyaluronic acid, heparin, heparin sulfate, chondroitin 6-sulfate, chondroitin 4-sulfate, dermatan sulfate, and keratin sulfate. Other GAGs are suitable for forming the matrix described herein, and those skilled in the art will either know or be able to ascertain other suitable GAGs using no more than routine experimentation. For a more detailed description of mucopolysaccharides, see Aspinall, *Polysaccharides*, Pergamon Press, Oxford (1970). For example, as disclosed in U.S. application Ser. No. 529,852, chondroitin-6-sulfate can be used where endochondral bone formation is desired. Heparin sulfate, on the other hand, may be used to formulate synthetic matrices for use in lung tissue repair.

Collagen can be reacted with a GAG in aqueous acidic solutions, preferably in diluted acetic acid solutions. By adding the GAG dropwise into the aqueous collagen dispersion, coprecipitates of tangled collagen fibrils coated with GAG results. This tangled mass of fibers then can be homogenized to form a homogeneous dispersion of fine fibers and then filtered and dried.

Insolubility of the collagen-GAG products can be raised to the desired degree by covalently crosslinking these materials, which also serves to raise the resistance to resorption of these materials. In general, any covalent cross-linking method suitable for cross-linking collagen also is suitable for cross-linking these composite materials, although crosslinking by a dehydrothermal process is preferred.

When dry, the crosslinked particles are essentially spherical, with diameters of about 500 μm. Scanning electron miscroscopy shows pores of about 20 μm on the surface and 40 μm on the interior. The interior is made up of both fibrous and sheet-like structures, providing surfaces for cell attachment. The voids interconnect, providing access to the cells throughout the interior of the particle. The material appears to be roughly 99.5% void volume, making the material very efficient in terms of the potential cell mass that can be grown per gram of microcarrier.

The morphogens described herein can be combined and dispersed in an appropriately modified tissue-specific matrix using any of the methods described below:

1. Ethanol Precipitation

Matrix is added to the morphogen dissolved in guanidine-HCl. Samples are vortexed and incubated at a low temperature. Samples are then further vortexed. Cold absolute ethanol is added to the mixture which is then stirred and incubated. After centrifugation (microfuge, high speed) the supernatant is discarded. The matrix is washed with cold concentrated ethanol in water and then lyophilized.

2. Acetonitrile Trifluoroacetic Acid Lyophilization

In this procedure, morphogen in an acetonitrile trifluoroacetic acid (ACN/TFA solution is added to the carrier material. Samples are vigorously vortexed many times and then lyophilized.

3. Buffered Saline Lyophilization

Morphogen preparations in physiological saline may also be vortexed with the matrix and lyophilized to produce morphogenically active material.

Bioassay

The following sets forth various procedures for evaluating the in vivo morphogenic utility of the morphogens and morphogenic compositions of this invention. The proteins and compositions may be injected or surgically implanted in a mammal, following any of a number of procedures well known in the art. For example, surgical implant bioassays may be performed essentially following the procedure of Sampath et al. (1983) *PNAS* 80:6591–6595.

Histological Evaluation

Histological sectioning and staining is preferred to determine the extent of morphogenesis in vivo, particularly in tissue repair procedures. Excised implants are fixed in Bouins Solution, embedded in paraffin, and cut into 6–8 µm sections. Staining with toluidine blue or hemotoxylin/eosin demonstrates clearly the ultimate development of the new tissue. Twelve day implants are usually sufficient to determine whether the implants contain newly induced tissue.

Successful implants exhibit a controlled progression through the stages of induced tissue development allowing one to identify and follow the tissue-specific events that occur. For example, in endochondral bone formation the stages include: (1) leukocytes on day one; (2) mesenchymal cell migration and proliferation on days two and three; (3) chondrocyte appearance on days five and six; (4) cartilage matrix formation on day seven; (5) cartilage calcification on day eight; (6) vascular invasion, appearance of osteoblasts, and formation of new bone on days nine and ten; (7) appearance of osteoblastic and bone remodeling and dissolution of the implanted matrix on days twelve to eighteen; and (8) hematopoietic bone marrow differentiation in the ossicle on day twenty-one.

Biological Markers

In addition to histological evaluation, biological markers may be used as a marker for tissue morphogenesis. Useful markers include tissue-specific enzymes whose activities may be assayed (e.g., spectrophotometrically) after homogenization of the implant. These assays may be useful for quantitation and for obtaining an estimate of tissue formation quickly after the implants are removed from the animal. For example, alkaline phosphatase activity may be used as a marker for osteogenesis.

Incorporation of systemically provided morphogens may be followed using tagged morphogens (e.g., radioactively labelled) and determining their localization in new tissue, and/or by monitoring their disappearance from the circulatory system using a standard pulse-chase labeling protocol. The morphogen also may be provided with a tissue-specific molecular tag, whose uptake may be monitored and correlated with the concentration of morphogen provided. As an example, ovary removal in female rats results in reduced bone alkaline phosphatase activity, rendering the rats predisposed to osteoporosis. If the female rats now are provided with a morphogen, e.g., OP-1, a reduction in the systemic concentration of calcium ($CA^{2+}$) is seen, which correlates with the presence of the provided morphogen and can be shown to correspond to increased alkaline phosphatase activity.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method of inducing kidney tissue growth in a mammal comprising contacting said kidney tissue with a morphogen such that the morphogen, when contacted with the kidney tissue, is capable of inducing the developmental cascade of tissue morphogenesis in said kidney tissue; wherein said morphogen has an amino acid sequence selected from:
   (a) a sequence having at least 70% homology with the C-terminal seven-cysteine skeleton of human OP-1, amino acids 38–139 of SEQ ID NO: 5;
   (b) an amino acid substitution variant defined by Generic Sequence 3, SEQ ID NO: 3;
   (c) an amino acid substitution variant defined by Generic Sequence 4, SEQ ID NO: 4; and,
and wherein said morphogen induces endochondral bone formation in an in vivo assay and induces kidney tissue growth.

2. A method for inducing kidney morphogenesis, comprising contacting kidney tissue with a morphogen; wherein said morphogen an amino acid sequence selected from:
   (a) a sequence having at least 70% homology with the C-terminal seven-cysteine skeleton of human OP-1, amino acids 38–139 of SEQ ID NO: 5;
   (b) an amino acid substitution variant defined by Generic Sequence 3, SEQ ID NO: 3; and
   (c) an amino acid substitution variant defined by Generic Sequence 4, SEQ ID NO: 4;
wherein said morphogen induces endochondral bone formation in an in vivo assay and induces morphogenesis of kidney tissue.

3. A method for repairing a damaged kidney tissue, comprising contacting kidney tissue with a morphogen; wherein said morphogen has an amino acid sequence selected from:
   (a) a sequence having at least 70% homology with the C-terminal seven-cysteine skeleton of human OP-1, amino acids 38–139 of SEQ ID NO: 5;
   (b) an amino acid substitution variant defined by Generic Sequence 3, SEQ ID NO: 3; and
   (c) an amino acid substitution variant defined by Generic Sequence 4, SEQ ID NO: 4;
wherein said morphogen induces endochondral bone formation in an in vivo assay and repairs damaged kidney tissue.

4. A method for treating a subject afflicted with damaged kidney tissue, comprising administering to the subject a morphogen, wherein said morphogen has an amino acid sequence selected from:

(a) a sequence having at least 70% homology with the C-terminal seven-cysteine skeleton of human OP-1, amino acids 38–139 of SEQ ID NO: 5;
(b) an amino acid substitution variant defined by Generic Sequence 3, SEQ ID NO: 3; and
(c) an amino acid substitution variant defined by Generic Sequence 4, SEQ ID NO: 4;

wherein said morphogen induces endochondral bone formation in an in vivo assay and induces kidney tissue growth.

5. The method of any one of claims 1, 2, 3 or 4, wherein the morphogen is selected from: OP-1, OP-2, BMP-2, BMP-4, BMP-5, BMP-6, Vg1, Vgr-1, DPP, 60A, or GDF-1.

6. The method of any one of claims 1, 2, 3 or 4, wherein the morphogen is OP-1.

7. The method of any one of claims 1, 2, 3 or 4, wherein the morphogen comprises the C-terminal seven-cysteine skeleton of human OP-1, amino acids 38–139 of SEQ ID NO: 51.

8. The method of any one of claims 1, 2, 3 or 4, wherein the morphogen has a sequence having at least 70% homology with the C-terminal seven-cysteine skeleton of human OP-1, amino acids 38–139 of SEQ ID NO: 51.

\* \* \* \* \*

SEQUENCE LISTING

<160> NUMBER OF SEQ ID NOS: 16

<210> SEQ ID NO 1
<211> LENGTH: 97
<212> TYPE: PRT
<213> ORGANISM: Artificial Sequence
<220> FEATURE:
<221> NAME/KEY: VARIANT
<222> LOCATION: (1)..(97)
<223> OTHER INFORMATION: wherein each Xaa  independently indicates one
      of the 20 natural L-isomers amino acids or a
      derivative thereof
<220> FEATURE:
<223> OTHER INFORMATION: generic sequence 1

<400> SEQUENCE: 1

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Cys Xaa Xaa Xaa Cys Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Cys Cys Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Cys Xaa Cys
                85                  90                  95

Xaa

<210> SEQ ID NO 2
<211> LENGTH: 97
<212> TYPE: PRT
<213> ORGANISM: Artificial Sequence
<220> FEATURE:
<221> NAME/KEY: VARIANT
<222> LOCATION: (1)..(97)
<223> OTHER INFORMATION: wherein each Xaa independently indicates one of
      the 20 natural L-isomers amino acids or a
      derivative thereof
<220> FEATURE:
<223> OTHER INFORMATION: generic sequence 2

<400> SEQUENCE: 2

Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Cys Xaa Xaa Xaa Cys Xaa Xaa Xaa
             20                  25                  30

Xaa Xaa Xaa Cys Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Cys Cys Xaa Xaa
     50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Cys Xaa Cys
             85                  90                  95

Xaa

<210> SEQ ID NO 3
<211> LENGTH: 97
<212> TYPE: PRT
<213> ORGANISM: Artificial Sequence
<220> FEATURE:
<221> NAME/KEY: VARIANT
<222> LOCATION: (1)..(97)
<223> OTHER INFORMATION: wherein each Xaa  is independently selected
      from a group of one or more specified amino acids as
      defined in the specification
<220> FEATURE:
<223> OTHER INFORMATION: generic sequence 3

<400> SEQUENCE: 3

Leu Tyr Val Xaa Phe Xaa Xaa Xaa Gly Trp Xaa Xaa Trp Xaa Xaa Ala
  1               5                  10                  15

Pro Xaa Gly Xaa Xaa Ala Xaa Tyr Cys Xaa Gly Xaa Cys Xaa Xaa Pro
             20                  25                  30

Xaa Xaa Xaa Xaa Xaa Xaa Xaa Xaa Asn His Ala Xaa Xaa Xaa Xaa Leu
         35                  40                  45

Xaa Xaa Xaa Xaa Xaa Xaa Xaa Xaa Xaa Xaa Xaa Xaa Cys Cys Xaa Pro
     50                  55                  60

Xaa Xaa Xaa Xaa Xaa Xaa Xaa Xaa Leu Xaa Xaa Xaa Xaa Xaa Xaa Xaa
 65                  70                  75                  80

Val Xaa Leu Xaa Xaa Xaa Xaa Xaa Met Xaa Val Xaa Xaa Cys Gly Cys
             85                  90                  95

Xaa

<210> SEQ ID NO 4
<211> LENGTH: 102
<212> TYPE: PRT

```
<213> ORGANISM: Artificial Sequence
<220> FEATURE:
<221> NAME/KEY: VARIANT
<222> LOCATION: (1)..(102)
<223> OTHER INFORMATION: wherein each Xaa is independently selected
      from a group of one or more specified amino acids as
      defined in the specification
<220> FEATURE:
<223> OTHER INFORMATION: generic sequence 4

<400> SEQUENCE: 4

Cys Xaa Xaa Xaa Xaa Leu Tyr Val Xaa Phe Xaa Xaa Xaa Gly Trp Xaa
 1               5                  10                  15

Xaa Trp Xaa Xaa Ala Pro Xaa Gly Xaa Xaa Ala Xaa Tyr Cys Xaa Gly
             20                  25                  30

Xaa Cys Xaa Xaa Pro Xaa Xaa Xaa Xaa Xaa Xaa Xaa Asn His Ala
         35                  40                  45

Xaa Xaa Xaa Xaa Leu Xaa Xaa Xaa Xaa Xaa Xaa Xaa Xaa Xaa Xaa
         50                  55                  60

Xaa Cys Cys Xaa Pro Xaa Xaa Xaa Xaa Xaa Xaa Xaa Leu Xaa Xaa
 65              70                  75                  80

Xaa Xaa Xaa Xaa Xaa Val Xaa Leu Xaa Xaa Xaa Xaa Xaa Met Xaa Val
             85                  90                  95

Xaa Xaa Cys Gly C

```
Ser Thr Gly Gly Lys Gln Arg Ser Gln Asn Arg Ser Lys Thr Pro Lys
  1               5                  10                  15

Asn Gln Glu Ala Leu Arg Met Ala Ser Val Ala Glu Asn Ser Ser Ser
             20                  25                  30

Asp Gln Arg Gln Ala Cys Lys Lys His Glu Leu Tyr Val Ser Phe Arg
         35                  40                  45

Asp Leu Gly Trp Gln Asp Trp Ile Ile Ala Pro Glu Gly Tyr Ala Ala
     50                  55                  60

Tyr Tyr Cys Glu Gly Glu Cys Ala Phe Pro Leu Asn Ser Tyr Met Asn
 65                  70                  75                  80

Ala Thr Asn His Ala Ile Val Gln Thr Leu Val His Phe Ile Asn Pro
                 85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Asn Val Ile Leu Lys Lys Tyr
            115                 120                 125

Arg Asn Met Val Val Arg Ala Cys Gly Cys His
        130                 135
```

```
<210> SEQ ID NO 7
<211> LENGTH: 139
<212> TYPE: PRT
<213> ORGANISM: Homo sapiens
<220> FEATURE:
<223> OTHER INFORMATION: tissue type hippocampus HOP2-MATURE

<400> SEQUENCE: 7
```

```
Ala Val Arg Pro Leu Arg Arg Arg Gln Pro Lys Lys Ser Asn Glu Leu
  1               5                  10                  15

Pro Gln Ala Asn Arg Leu Pro Gly Ile Phe Asp Asp Val His Gly Ser
             20                  25                  30

His Gly Arg Gln Val Cys Arg Arg His Glu Leu Tyr Val Ser Phe Gln
         35                  40                  45

Asp Leu Gly Trp Leu Asp Trp Val Ile Ala Pro Gln Gly Tyr Ser Ala
     50                  55                  60

Tyr Tyr Cys Glu Gly Glu Cys Ser Phe Pro Leu Asp Ser Cys Met Asn
 65                  70                  75                  80

Ala Thr Asn His Ala Ile Leu Gln Ser Leu Val His Leu Met Lys Pro
                 85                  90                  95

Asn Ala Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys Ala
            115                 120                 125

Arg Asn Met Val Val Lys Ala Cys Gly Cys His
        130                 135
```

```
<210> SEQ ID NO 8
<211> LENGTH: 139
<212> TYPE: PRT
<213> ORGANISM: Murinae gen. sp.
<220> FEATURE:
<223> OTHER INFORMATION: tissue type embyro MOP2-MATURE

<400> SEQUENCE: 8
```

```
Ala Ala Arg Pro Leu Lys Arg Arg Gln Pro Lys Lys Thr Asn Glu Leu
  1               5                  10                  15

Pro His Pro Asn Lys Leu Pro Gly Ile Phe Asp Asp Gly His Gly Ser
```

-continued

```
                    20                  25                  30
Arg Gly Arg Glu Val Cys Arg His Glu Leu Tyr Val Arg Phe Arg
             35                  40                  45
Asp Leu Gly Trp Leu Asp Trp Val Ile Ala Pro Gln Gly Tyr Ser Ala
         50                  55                  60
Tyr Tyr Cys Glu Gly Glu Cys Ala Phe Pro Leu Asp Ser Cys Met Asn
 65                  70                  75                  80
Ala Thr Asn His Ala Ile Leu Gln Ser Leu Val His Leu Met Lys Pro
                 85                  90                  95
Asp Val Val Pro Lys Ala Cys Cys Ala Pro Thr Lys Leu Ser Ala Thr
             100                 105                 110
Ser Val Leu Tyr Tyr Asp Ser Ser Asn Val Ile Leu Arg Lys His
         115                 120                 125
Arg Asn Met Val Val Lys Ala Cys Gly Cys His
 130                 135
```

<210> SEQ ID NO 9
<211> LENGTH: 101
<212> TYPE: PRT
<213> ORGANISM: bovinae
<220> FEATURE:
<223> OTHER INFORMATION: CBMP-2A-FX

<400> SEQUENCE: 9

```
Cys Lys Arg His Pro Leu Tyr Val Asp Phe Ser Asp Val Gly Trp Asn
  1               5                  10                  15
Asp Trp Ile Val Ala Pro Pro Gly Tyr His Ala Phe Tyr Cys His Gly
                 20                  25                  30
Glu Cys Pro Phe Pro Leu Ala Asp His Leu Asn Ser Thr Asn His Ala
             35                  40                  45
Ile Val Gln Thr Leu Val Asn Ser Val Asn Ser Lys Ile Pro Lys Ala
         50                  55                  60
Cys Cys Val Pro Thr Glu Leu Ser Ala Ile Ser Met Leu Tyr Leu Asp
 65                  70                  75                  80
Glu Asn Glu Lys Val Val Leu Lys Asn Tyr Gln Asp Met Val Val Glu
                 85                  90                  95
Gly Cys Gly Cys Arg
            100
```

<210> SEQ ID NO 10
<211> LENGTH: 101
<212> TYPE: PRT
<213> ORGANISM: Homo sapiens
<220> FEATURE:
<223> OTHER INFORMATION: tissue type hippocampus CMBP-2B-FX

<400> SEQUENCE: 10

```
Cys Arg Arg His Ser Leu Tyr Val Asp Phe Ser Asp Val Gly Trp Asn
  1               5                  10                  15
Asp Trp Ile Val Ala Pro Pro Gly Tyr Gln Ala Phe Tyr Cys His Gly
                 20                  25                  30
Asp Cys Pro Phe Pro Leu Ala Asp His Leu Asn Ser Thr Asn His Ala
             35                  40                  45
Ile Val Gln Thr Leu Val Asn Ser Val Asn Ser Ser Ile Pro Lys Ala
         50                  55                  60
Cys Cys Val Pro Thr Glu Leu Ser Ala Ile Ser Met Leu Tyr Leu Asp
 65                  70                  75                  80
```

-continued

Glu Tyr Asp Lys Val Val Leu Lys Asn Tyr Gln Met Val Val Glu
                85                  90                  95

Gly Cys Gly Cys Arg
        100

<210> SEQ ID NO 11
<211> LENGTH: 102
<212> TYPE: PRT
<213> ORGANISM: Drosophila melanogaster
<220> FEATURE:
<223> OTHER INFORMATION: DPP-FX

<400> SEQUENCE: 11

Cys Arg Arg His Ser Leu Tyr Val Asp Phe Ser Asp Val Gly Trp Asp
  1               5                  10                  15

Asp Trp Ile Val Ala Pro Leu Gly Tyr Asp Ala Tyr Tyr Cys His Gly
             20                  25                  30

Lys Cys Pro Phe Pro Leu Ala Asp His Phe Asn Ser Thr Asn His Ala
         35                  40                  45

Val Val Gln Thr Leu Val Asn Asn Asn Asn Pro Gly Lys Val Pro Lys
     50                  55                  60

Ala Cys Cys Val Pro Thr Gln Leu Asp Ser Val Ala Met Leu Tyr Leu
 65                  70                  75                  80

Asn Asp Gln Ser Thr Val Val Leu Lys Asn Tyr Gln Glu Met Thr Val
                85                  90                  95

Val Gly Cys Gly Cys Arg
            100

<210> SEQ ID NO 12
<211> LENGTH: 102
<212> TYPE: PRT
<213> ORGANISM: Xenopus sp.
<220> FEATURE:
<223> OTHER INFORMATION: VGL-FX

<400> SEQUENCE: 12

Cys Lys Lys Arg His Leu Tyr Val Glu Phe Lys Asp Val Gly Trp Gln
  1               5                  10                  15

Asn Trp Val Ile Ala Pro Gln Gly Tyr Met Ala Asn Tyr Cys Tyr Gly
             20                  25                  30

Glu Cys Pro Tyr Pro Leu Thr Glu Ile Leu Asn Gly Ser Asn His Ala
         35                  40                  45

Ile Leu Gln Thr Leu Val His Ser Ile Glu Pro Glu Asp Ile Pro Leu
     50                  55                  60

Pro Cys Cys Val Pro Thr Lys Met Ser Pro Ile Ser Met Leu Phe Tyr
 65                  70                  75                  80

Asp Asn Asn Asp Asn Val Val Leu Arg His Tyr Glu Asn Met Ala Val
                85                  90                  95

Asp Glu Cys Gly Cys Arg
            100

<210> SEQ ID NO 13
<211> LENGTH: 102
<212> TYPE: PRT
<213> ORGANISM: Murinae gen. sp.
<220> FEATURE:
<223> OTHER INFORMATION: VGR-1-FX

<400> SEQUENCE: 13

Cys Lys Lys His Gly Leu Tyr Val Ser Phe Gln Asp Val Gly Trp Gln

```
  1               5              10              15
Asp Trp Ile Ile Ala Pro Lys Gly Tyr Ala Ala Asn Tyr Cys Asp Gly
            20                  25                  30

Glu Cys Ser Phe Pro Leu Asn Ala His Met Asn Ala Thr Asn His Ala
        35                  40                  45

Ile Val Gln Thr Leu Val His Val Met Asn Pro Glu Tyr Val Pro Lys
    50                  55                  60

Pro Cys Cys Ala Pro Thr Lys Val Asn Ala Ile Ser Val Leu Tyr Phe
65                  70                  75                  80

Asp Asp Asn Ser Asn Val Ile Leu Lys Lys Tyr Arg Asn Met Val Val
                85                  90                  95

Arg Ala Cys Gly Cys His
            100
```

<210> SEQ ID NO 14
<211> LENGTH: 106
<212> TYPE: PRT
<213> ORGANISM: Homo sapiens
<220> FEATURE:
<223> OTHER INFORMATION: tissue type BRAIN GDF-1 (fx)

<400> SEQUENCE: 14

```
Cys Arg Ala Arg Arg Leu Tyr Val Ser Phe Arg Glu Val Gly Trp His
  1               5                  10                  15

Arg Trp Val Ile Ala Pro Arg Gly Phe Leu Ala Asn Tyr Cys Gln Gly
            20                  25                  30

Gln Cys Ala Leu Pro Val Ala Leu Ser Gly Ser Gly Gly Pro Pro Ala
        35                  40                  45

Leu Asn His Ala Val Leu Arg Ala Leu Met His Ala Ala Ala Pro Gly
    50                  55                  60

Ala Ala Asp Leu Pro Cys Cys Val Pro Ala Arg Leu Ser Pro Ile Ser
65                  70                  75                  80

Val Leu Phe Phe Asp Asn Ser Asp Asn Val Val Leu Arg Gln Tyr Glu
                85                  90                  95

Asp Met Val Val Asp Glu Cys Gly Cys Arg
            100                 105
```

<210> SEQ ID NO 15
<211> LENGTH: 1873
<212> TYPE: DNA
<213> ORGANISM: Murinae gen. sp.
<220> FEATURE:
<221> NAME/KEY: CDS
<222> LOCATION: (104)..(1393)
<223> OTHER INFORMATION: osteogenic protein MOP1, MOP1 cDNA
<223> OTHER INFORMATION: tissue type embryo

<400> SEQUENCE: 15

```
ctgcagcaag tgacctcggg tcgtggaccg ctgccctgcc cctccgctg ccacctgggg        60 cggcgcgggc ccggtgcccc ggatcgcgcg tagagccggc gcg atg cac gtg cgc       115
                                             Met His Val Arg
                                               1 tcg ctg cgc gct gcg gcg cca cac agc ttc gtg gcg ctc tgg gcg cct       163
Ser Leu Arg Ala Ala Ala Pro His Ser Phe Val Ala Leu Trp Ala Pro
  5                  10                  15                  20 ctg ttc ttg ctg cgc tcc gcc ctg gcc gat ttc agc ctg gac aac gag       211
Leu Phe Leu Leu Arg Ser Ala Leu Ala Asp Phe Ser Leu Asp Asn Glu
                25                  30                  35 gtg cac tcc agc ttc atc cac cgg cgc ctc cgc agc cag gag cgg cgg       259
```

```
Val His Ser Ser Phe Ile His Arg Arg Leu Arg Ser Gln Glu Arg Arg
            40                  45                  50 gag atg cag cgg gag atc ctg tcc atc tta ggg ttg ccc cat cgc ccg      307
Glu Met Gln Arg Glu Ile Leu Ser Ile Leu Gly Leu Pro His Arg Pro
        55                  60                  65 cgc ccg cac ctc cag gga aag cat aat tcg gcg ccc atg ttc atg ttg      355
Arg Pro His Leu Gln Gly Lys His Asn Ser Ala Pro Met Phe Met Leu
    70                  75                  80 gac ctg tac aac gcc atg gcg gtg gag gag agc ggg ccg gac gga cag      403
Asp Leu Tyr Asn Ala Met Ala Val Glu Glu Ser Gly Pro Asp Gly Gln
85                  90                  95                  100 ggc ttc tcc tac ccc tac aag gcc gtc ttc agt acc cag ggc ccc cct      451
Gly Phe Ser Tyr Pro Tyr Lys Ala Val Phe Ser Thr Gln Gly Pro Pro
                105                 110                 115 tta gcc agc ctg cag gac agc cat ttc ctc act gac gcc gac atg gtc      499
Leu Ala Ser Leu Gln Asp Ser His Phe Leu Thr Asp Ala Asp Met Val
            120                 125                 130 atg agc ttc gtc aac cta gtg gaa cat gac aaa gaa ttc ttc cac cct      547
Met Ser Phe Val Asn Leu Val Glu His Asp Lys Glu Phe Phe His Pro
        135                 140                 145 cga tac cac cat cgg gag ttc cgg ttt gat ctt tcc aag atc ccc gag      595
Arg Tyr His His Arg Glu Phe Arg Phe Asp Leu Ser Lys Ile Pro Glu
    150                 155                 160 ggc gaa cgg gtg acc gca gcc gaa ttc agg atc tat aag gac tac atc      643
Gly Glu Arg Val Thr Ala Ala Glu Phe Arg Ile Tyr Lys Asp Tyr Ile
165                 170                 175                 180 cgg gag cga ttt gac aac gag acc ttc cag atc aca gtc tat cag tgg      691
Arg Glu Arg Phe Asp Asn Glu Thr Phe Gln Ile Thr Val Tyr Gln Trp
                185                 190                 195 ctc cag gag cac tca ggc agg gag tcg gac ctc ttc ttg ctg gac agc      739
Leu Gln Glu His Ser Gly Arg Glu Ser Asp Leu Phe Leu Leu Asp Ser
            200                 205                 210 cgc acc atc tgg gct tct gag gag ggc tgg ttg gtg ttt gat atc aca      787
Arg Thr Ile Trp Ala Ser Glu Glu Gly Trp Leu Val Phe Asp Ile Thr
        215                 220                 225 gcc acc agc aac cac tgg gtg gtc aac cct cgg cac aac ctg ggc tta      835
Ala Thr Ser Asn His Trp Val Val Asn Pro Arg His Asn Leu Gly Leu
    230                 235                 240 cag ctc tct gtg gag acc ctg gat ggg cag agc atc aac ccc aag ttg      883
Gln Leu Ser Val Glu Thr Leu Asp Gly Gln Ser Ile Asn Pro Lys Leu
245                 250                 255                 260 gca ggc ctg att gga cgg cat gga ccc cag aac aag caa ccc ttc atg      931
Ala Gly Leu Ile Gly Arg His Gly Pro Gln Asn Lys Gln Pro Phe Met
                265                 270                 275 gtg gcc ttc ttc aag gcc acg gaa gtc cat ctc cgt agt atc cgg tcc      979
Val Ala Phe Phe Lys Ala Thr Glu Val His Leu Arg Ser Ile Arg Ser
            280                 285                 290 acg ggg ggc aag cag cgc agc cag aat cgc tcc aag acg cca aag aac     1027
Thr Gly Gly Lys Gln Arg Ser Gln Asn Arg Ser Lys Thr Pro Lys Asn
        295                 300                 305 caa gag gcc ctg agg atg gcc agt gtg gca gaa aac agc agc agt gac     1075
Gln Glu Ala Leu Arg Met Ala Ser Val Ala Glu Asn Ser Ser Ser Asp
    310                 315                 320 cag agg cag gcc tgc aag aaa cat gag ctg tac gtc agc ttc cga gac     1123
Gln Arg Gln Ala Cys Lys Lys His Glu Leu Tyr Val Ser Phe Arg Asp
325                 330                 335                 340 ctt ggc tgg cag gac tgg atc att gca cct gaa ggc tat gct gcc tac     1171
Leu Gly Trp Gln Asp Trp Ile Ile Ala Pro Glu Gly Tyr Ala Ala Tyr
                345                 350                 355
```

```
tac tgt gag gga gag tgc gcc ttc cct ctg aac tcc tac atg aac gcc      1219
Tyr Cys Glu Gly Glu Cys Ala Phe Pro Leu Asn Ser Tyr Met Asn Ala
        360                 365                 370 acc aac cac gcc atc gtc cag aca ctg gtt cac ttc atc aac cca gac      1267
Thr Asn His Ala Ile Val Gln Thr Leu Val His Phe Ile Asn Pro Asp
            375                 380                 385 aca gta ccc aag ccc tgc tgt gcg ccc acc cag ctc aac gcc atc tct      1315
Thr Val Pro Lys Pro Cys Cys Ala Pro Thr Gln Leu Asn Ala Ile Ser
390                 395                 400 gtc ctc tac ttc gac gac agc tct aat gtc gac ctg aag aag tac aga      1363
Val Leu Tyr Phe Asp Asp Ser Ser Asn Val Asp Leu Lys Lys Tyr Arg
405                 410                 415                 420 aac atg gtg gtc cgg gcc tgt ggc tgc cac tagctcttcc tgagaccctg        1413
Asn Met Val Val Arg Ala Cys Gly Cys His
                425                 430 acctttgcgg ggccacacct ttccaaatct tcgatgtctc accatctaag tctctcactg    1473
cccaccttgg cgaggagaac agaccaacct ctcctgagcc ttccctcacc tcccaaccgg    1533
aagcatgtaa gggttccaga aacctgagcg tgcagcagct gatgagcgcc ctttccttct    1593
ggcacgtgac ggacaagatc ctaccagcta ccacagcaaa cgcctaagag caggaaaaat    1653
gtctgccagg aaagtgtcca gtgtccacat ggcccctggc gctctgagtc tttgaggagt    1713
aatcgcaagc tcgttcagc tgcagcagaa ggaagggctt agccagggtg ggcgctggcg     1773
tctgtgttga agggaaacca agcagaagcc actgtaatga tatgtcacaa taaaacccat    1833
gaatgaaaaa aaaaaaaaaa aaaaaaaaaa aaaagaattc                          1873
```

<210> SEQ ID NO 16
<211> LENGTH: 430
<212> TYPE: PRT
<213> ORGANISM: Murinae gen. sp.

<400> SEQUENCE: 16

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Ser Gly
                85                  90                  95

Pro Asp Gly Gln Gly Phe Ser Tyr Pro Tyr Lys Ala Val Phe Ser Thr
            100                 105                 110

Gln Gly Pro Pro Leu Ala Ser Leu Gln Asp Ser His Phe Leu Thr Asp
        115                 120                 125

Ala Asp Met Val Met Ser Phe Val Asn Leu Val Glu His Asp Lys Glu
    130                 135                 140

Phe Phe His Pro Arg Tyr His His Arg Glu Phe Arg Phe Asp Leu Ser
145                 150                 155                 160

Lys Ile Pro Glu Gly Glu Arg Val Thr Ala Ala Glu Phe Arg Ile Tyr
                165                 170                 175

Lys Asp Tyr Ile Arg Glu Arg Phe Asp Asn Glu Thr Phe Gln Ile Thr
            180                 185                 190

```
Val Tyr Gln Trp Leu Gln Glu His Ser Gly Arg Glu Ser Asp Leu Phe
        195                 200                 205

Leu Leu Asp Ser Arg Thr Ile Trp Ala Ser Glu Glu Gly Trp Leu Val
        210                 215                 220

Phe Asp Ile Thr Ala Thr Ser Asn His Trp Val Val Asn Pro Arg His
225                 230                 235                 240

Asn Leu Gly Leu Gln Leu Ser Val Glu Thr Leu Asp Gly Gln Ser Ile
                245                 250                 255

Asn Pro Lys Leu Ala Gly Leu Ile Gly Arg His Gly Pro Gln Asn Lys
                260                 265                 270

Gln Pro Phe Met Val Ala Phe Phe Lys Ala Thr Glu Val His Leu Arg
            275                 280                 285

Ser Ile Arg Ser Thr Gly Gly Lys Gln Arg Ser Gln Asn Arg Ser Lys
        290                 295                 300

Thr Pro Lys Asn Gln Glu Ala Leu Arg Met Ala Ser Val Ala Glu Asn
305                 310                 315                 320

Ser Ser Ser Asp Gln Arg Gln Ala Cys Lys Lys His Glu Leu Tyr Val
                325                 330                 335

Ser Phe Arg Asp Leu Gly Trp Gln Asp Trp Ile Ile Ala Pro Glu Gly
                340                 345                 350

Tyr Ala Ala Tyr Tyr Cys Glu Gly Glu Cys Ala Phe Pro Leu Asn Ser
                355                 360                 365

Tyr Met Asn Ala Thr Asn His Ala Ile Val Gln Thr Leu Val His Phe
        370                 375                 380

Ile Asn Pro Asp Thr Val Pro Lys Pro Cys Cys Ala Pro Thr Gln Leu
385                 390                 395                 400

Asn Ala Ile Ser Val Leu Tyr Phe Asp Asp Ser Ser Asn Val Asp Leu
                405                 410                 415

Lys Lys Tyr Arg Asn Met Val Val Arg Ala Cys Gly Cys His
            420                 425                 430
```